US011311525B2

(12) United States Patent
Fendt et al.

(10) Patent No.: US 11,311,525 B2
(45) Date of Patent: Apr. 26, 2022

(54) USE OF ALPHA 7 NICOTINIC ACETYLCHOLINE RECEPTOR AGONISTS

(71) Applicant: Novartis AG, Basel (CH)

(72) Inventors: Markus Fendt, Basel (CH); Dominik Feuerbach, Basel (CH); Sjoerd Johannes Finnema, Stockholm (SE); Christer Halldin, Stockholm (SE); Donald Johns, Cambridge, MA (US); Cristina Lopez-Lopez, Basel (CH); Kevin Hall McAllister, Basel (CH); Judit Sovago, Basel (CH); Markus Weiss, Basel (CH)

(73) Assignee: Novartis AG, Basel (CH)

(*) Notice: Subject to any disclaimer, the term of this patent is extended or adjusted under 35 U.S.C. 154(b) by 174 days.

(21) Appl. No.: 15/686,919

(22) Filed: Aug. 25, 2017

(65) Prior Publication Data
US 2017/0348294 A1 Dec. 7, 2017

Related U.S. Application Data

(63) Continuation of application No. 14/799,744, filed on Jul. 15, 2015, now abandoned, which is a continuation of application No. PCT/IB2014/058225, filed on Jan. 13, 2014, and a continuation of application No. PCT/IB2014/058224, filed on Jan. 13, 2014, and a continuation of application No. PCT/IB2013/050368, filed on Jan. 15, 2013.

(60) Provisional application No. 61/752,765, filed on Jan. 15, 2013, provisional application No. 61/752,772, filed on Jan. 15, 2013.

(51) Int. Cl.
| | |
|---|---|
| A61K 31/444 | (2006.01) |
| A61K 9/00 | (2006.01) |
| A61K 45/06 | (2006.01) |
| A61K 47/02 | (2006.01) |
| A61K 31/08 | (2006.01) |
| A61K 31/135 | (2006.01) |

(52) U.S. Cl.
CPC .......... *A61K 31/444* (2013.01); *A61K 9/0019* (2013.01); *A61K 31/08* (2013.01); *A61K 31/135* (2013.01); *A61K 45/06* (2013.01); *A61K 47/02* (2013.01)

(58) Field of Classification Search
CPC .............. A61K 31/444; A61K 31/4545; A61K 31/501; A61K 31/506; A61K 31/55
See application file for complete search history.

(56) References Cited

U.S. PATENT DOCUMENTS

| | | | |
|---|---|---|---|
| 7,579,362 B2 | 8/2009 | Feuerbach et al. | |
| 2007/0249617 A1* | 10/2007 | Feuerbach | C07D 453/02 |
| | | | 514/252.03 |
| 2013/0310422 A1* | 11/2013 | Brown | A61K 31/13 |
| | | | 514/317 |

FOREIGN PATENT DOCUMENTS

| | | |
|---|---|---|
| CN | 1965968 A | 5/2007 |
| CN | 200510045087 A | 5/2007 |
| WO | 0185727 A1 | 11/2001 |
| WO | 2004016608 A1 | 2/2004 |
| WO | 2004022556 A1 | 3/2004 |
| WO | 2004029050 A1 | 4/2004 |
| WO | 2005123732 A1 | 12/2005 |
| WO | 2006005608 A1 | 1/2006 |
| WO | 2007045478 A1 | 4/2007 |
| WO | 2007068475 A1 | 6/2007 |
| WO | 2007068476 A1 | 6/2007 |
| WO | 2007093602 A1 | 8/2007 |
| WO | 2009018505 A1 | 2/2009 |
| WO | 2010009290 A1 | 1/2010 |
| WO | 2010056622 A1 | 5/2010 |
| WO | 2010085724 A1 | 7/2010 |
| WO | 2011009890 A2 | 1/2011 |
| WO | 2011036167 A1 | 3/2011 |
| WO | 2012062319 A1 | 5/2012 |
| WO | 2012101060 A1 | 8/2012 |
| WO | 2013002365 A1 | 3/2013 |

OTHER PUBLICATIONS

Menoufiya et al, AAMJ, vol. 10, N. 3, Sep. 2012, Suppl-3. (Year: 2012).*
Office Action for Korean Patent Application No. 10-2015-7021931 dated Oct. 11, 2016, 16 pages.
Zen'ichiro et al., "Severe Lightning Pain After Subarachnoid Block in a Patient With Neuropathic Pain of Central Origin: Which Drug is Best to Treat the Pain?" Clnical Journal of Pain, Sep. 2000, vol. 16, Issue 3, 2 pages.
Alkire et al. "Thalamic Microinjection of Nicotine Reverses Sevoflurane-induced Loss of Righting Reflex in the Rat", Anesthesiology, vol. 107 No. 2, 2007, p. 264-272.
Kalivas, "Histamine-Induced Arousal in the Conscious and Pentobarbital Pretreated Rat" Journal of Pharmacology and Experimental Therapeutics, vol. 222 No. 1, 1982, p. 37-42.
Luo et al., "Basal Forebrain Histaminergic Transmission Modulates Electroencephalographic Activity and Emergence from Isoflurane Anesthesia", Anesthesiology, vol. 111 No. 4, 2009, p. 725-733.
Manual at Therapeutic Agents, 2007, p. 1787-1788; 1797-1798.
Saint-Mleux et al., "Nicotnic Enhancement of the Noradrenergic Inhibition of Sleep-Promoting Neurons in the Ventrolateral Preoptic Area", Journal of Neuroscience, vol. 24 No. 1, Jan. 7, 2007, p. 63-67.
Uteshev et al., "Somatic Ca2+ Dynamics in Response to Choline-Mediated Excitation in Histaminergic Tuberomammillary Neurons" Neuroscience vol. 134, 2005, p. 133-143.
Young et al., "Nicotine Improves Sustained Attention in Mice: Evidence for Involvement of the a7 Nicotinic Acetylcholine Receptor", Neuropsychopharmacology, vol. 29, 2004, p. 891-900.

(Continued)

*Primary Examiner* — Jean P Cornet
(74) *Attorney, Agent, or Firm* — Hoffman Warnick LLC

(57) ABSTRACT

The invention concerns the use of certain alpha 7 nicotinic acetylcholine receptor agonist for the facilitation of emergence from general anesthesia.

9 Claims, 4 Drawing Sheets

(56) References Cited

OTHER PUBLICATIONS

Notice of Reasons for Rejection and English Translation thereof for JP Application No. P2015-552186 dated Jun. 13, 2017, 14 pages.
Office Action and English Translation thereof for Japanese Patent Application No. P2015-552186 dated Aug. 9, 2016, 8 pages.
Office Action and English Translation thereof for Chinese Patent Application No. PAT055497-CN-PCT dated Oct. 24, 2016, 22 pages.
Afari et al., "Chronic Fatigue Syndrome: A Review," American Journal of Psychiatry, vol. 160, No. 2 (2003), pp. 221-236.
Arias et al., "Different Interaction between the Agonist JN403 and the Competitive Antagonist Methyllcaconitine with the Human alpha7 Nicotinic Acetylcholine Receptor," Biochemistry, vol. 49 (2010), pp. 4169-4180.
Banerjee et al., "Pharmacotherapy for excessive daytime sleepiness," Sleep Medicine Reviews, vol. 8, (2004), pp. 339-354.
Coates et al., "Thiopental is a Competitive Inhibitor at the Human alpha7 Nicotinic Acetylcholine Receptor," Anesthetic Analg., vol. 92, (2001), pp. 930-933.
Feuerbach et al., "The selective nicotinic acetylcholine receptor alpha7 agonist JN403 is active in animal models of cognition, sensory gating, epilepsy and pain," Neuropharmacology, vol. 56, (2009), pp. 254-263.
Gundisch et al., "Nicotinic acetylcholine receptor ligands, a patent review," Expert Opinion Therapeutic Patents, vol. 21, No. 12, (2011), pp. 1867-1896.
Houghton et al., "Pharmacotherapy for cataplexy," Sleep Medicine Reviews, vol. 8, (2004), pp. 355-366.
International Search Report and Written Opinion for International Application No. PCT/IB2013/050368, dated Jan. 15, 2013, 27 pgs.
International Search Report and Written Opinion for International Application No. PCT/IB2014/058224, dated Jan. 13, 2014, 31 pgs.
International Search Report and Written Opinion for International Application No. PCT/IB2014/058225, dated Jan. 13, 2014, 15 pgs.
Lammers et al., "Pharmacological management of narcolepsy," Expert Opinion Pharmacother. vol. 4, No. 10, (2003), pp. 1739-1746.
Mazurov et al., "Discovery and Development of alpha7 Nicotinic Acetylcholine Receptor Modulators," Journal of Medicinal Chemistry, vol. 54, (2011), pp. 7943-7961.
Suzuki et al., "Nitrous Oxide and Xenon Inhibit the Human (alpha 7)5 Nicotinic Acetylcholine Receptor Expressed in Xenopus Oocyte," Anesthesia and Analgesia, vol. 96, No. 2, (2003), pp. 443-448.
Tassonyi et al., "The role of nicotinic acetylcholine receptors in the mechanisms of anesthesia," Brain Research Bulletin, vol. 57, No. 2, (2002) pp. 133-150.
International Preliminary Report on Patentability for PCT/IB2014/058224, dated Jul. 30, 2015, 20 pages.
International Preliminary Report on Patentability for PCT/IB2014/050368, dated Jul. 30, 2015, 15 pages.
International Preliminary Report on Patentability for PCT/IB2014/058225, dated Jul. 30, 2015, 11 pages.

* cited by examiner

USE OF ALPHA 7 NICOTINIC ACETYLCHOLINE RECEPTOR AGONISTS

CROSS REFERENCE TO RELATED APPLICATIONS

This patent application is a continuation under 35 U.S.C. §120 of application Ser. No. 14/799,744, which was filed on Jul. 15, 2015, which is a continuation under 35 U.S.C. §§363, 365(c), and 120 of each of: International Application No. PCT/IB2014/058224, which was filed on 13 Jan. 2014 and which claims the benefit of U.S. Provisional Application No. 61/752,765, filed on 15 Jan. 2013; International Application No. PCT/IB2013/050368, which was filed on 15 Jan. 2013; and co-pending International Application No. PCT/IB2014/058225, which was filed on 13 Jan. 2014 and which claims the benefit of U.S. Provisional Application No. 61/752,772, filed on 15 Jan. 2013. Each of the foregoing applications is incorporated as though fully set forth herein.

BACKGROUND

The present invention relates to medical uses of alpha 7 nicotinic acetylcholine receptor (α7 nAChR) agonists.

Before surgical operations (in the perioperative period), patients are put under anesthesia; said anesthesia is maintained during surgical operations. There are two general types of anesthesia: general anesthesia and regional anesthesia. General anesthesia is typically performed during relatively large, complicated surgeries. In USA alone, nearly 60,000 patients per day receive general anesthesia for surgery (Brown E L et al, New England Journal of Medicine, 2010, 363, 2638-2650).

General anesthesia can be regarded as a reversible loss of consciousness caused by general anesthetics. General anesthesia is characterized by three periods: the induction period, the maintenance period, and the emergence period. In the induction period, the subject loses consciousness. Said loss of consciousness is maintained during the maintenance period. In the emergence period, the subject regains consciousness. Emergence from anesthesia is complete when the subject is (i) conscious, (ii) able to answer simple questions, (iii) able to make voluntary movements, (iv) maintains adequate ventilation and (v) is able to protect his airways.

Induction/maintenance of general anesthesia is an active process, wherein loss of consciousness is caused/maintained by treatment of patients with general anesthetics. In contrast, emergence from general anesthesia is a passive process whereby general anesthetics are merely discontinued, typically at the end of surgery.

Although the actions of many other drugs used in anesthesiology are pharmacologically reversed when no longer desired; e.g. muscle relaxants (e.g. sugammadex reversing the action of rocuronium) and opioids (e.g. naloxone as reversing agent); this is not the case for loss of consciousness induced by general anesthetics.

This current clinical practice of passive emergence can be dangerous because patients may be susceptible to potentially severe complications, e.g. laryngospasm, respiratory depression, hemodynamic instability, anesthesia-related delirium and postoperative cognitive dysfunction (POCD).

In addition, significant time and labor are spent by hospitals on the care of patients under general anesthesia in operating rooms/intensive care units.

Time for emergence from general anesthesia can be unpredictable as it depends on many factors related to the patient, the type of anesthetic given and the length of surgery. Depending on circumstances, this passive emergence from general anesthesia may take hours. Causes for slow emergence from anesthesia may include overdose; duration and type of anesthetic given; and potentiation by other drugs.

An overdose can be caused by e.g. delayed drug metabolism such as in renal or hepatic failure, and/or increased sensitivity to particular agents.

Duration and type of anesthetic given: for inhalational anesthetics the speed of emergence is directly related to alveolar ventilation. Therefore hypoventilation is a frequent cause of delayed emergence. For intravenous anaesthetic agents, immediate recovery depends mainly on redistribution from blood and brain into muscle and fat. Patients given propofol for induction and/or maintenance recover faster than those receiving other agents because propofol is rapidly metabolised by the liver and possibly also at other extrahepatic sites. Elimination half-life is relatively fast (10 to 70 minutes), and it does not accumulate. With thiopentone however, whilst the initial drug effect is terminated by redistribution within 5 to 15 minutes, elimination is by oxidative metabolism in the liver at a rate of 15% per hour. It therefore has a long elimination half-life of 3.4 to 22 hours and as much as 30% of the dose may remain in the body at 24 hours. Cumulative effects may therefore become apparent when more than one dose is given. For most other intravenous anaesthetic drugs the termination of drug action depends on the time required to metabolise or excrete the drug (elimination or metabolic half-life) and in this situation, advanced age or renal or hepatic disease can prolong drug action.

Potentiation by other drugs: prior ingestion of sedative premedication such as benzodiazepines, or alcohol, may potentiate the central nervous system depressant effects of anaesthetic and analgesic drugs, and may delay emergence from anaesthesia.

For these reasons, there is a need to provide agents useful for the facilitation of emergence from general anesthesia.

BRIEF DESCRIPTION OF THE INVENTION

It has been found that certain α7 nAChR agonists may be used for the facilitation of emergence from general anesthesia.

Accordingly, a first aspect of the invention concerns the use of an α7 nAChR agonist for the facilitation of emergence from general anesthesia;

wherein said α7 nAChR agonist is (i) a compound of formula (I)

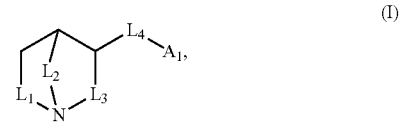

wherein $L_1$ is —$CH_2$—; $L_2$ is —$CH_2$—$CH_2$—; and $L_3$ is —$CH_2$— or —$CH(CH_3)$—; or $L_1$ is —$CH_2$—$CH_2$—; $L_2$ is —$CH_2$—; and $L_3$ is —$CH_2$—$CH_2$—;

$L_4$ is a group selected from

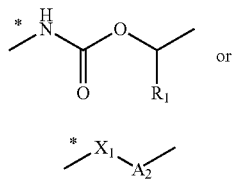

wherein the bond marked with the asterisk is attached to the azabicycloalkyl moiety;
$R_1$ is methyl;
$X_1$ is —O— or —NH—;
$A_2$ is selected from

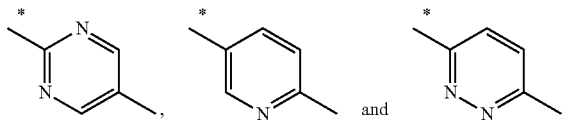

wherein the bond marked with the asterisk is attached to $X_1$;
$A_1$ is phenyl, indole or 1,3-dihydro-indol-2-one, which may be substituted once or more than once by $R_2$, each $R_2$ independently is $C_{1-6}$alkyl, $C_{1-6}$halogenalkyl or halogen; or
(ii) a compound selected from the group consisting of
4-(5-phenyl-1,3,4-thiadiazol-2-yloxy)-1azatricyclo [3.3.1.1$^{3,7}$decane];
(4S)-4-(5-phenyl-1,3,4-thiadiazol-2-yloxy)-1azatricyclo [3.3.1.1$^{3,7}$]decane;
4-(6-(1H-indol-5-yl)-pyridazin-3-yloxy)-1azatricyclo [3.3.1.1$^{3,7}$]decane;
4-(6-(1H-indol-5-yl)-pyridin-3-yloxy)-1azatricyclo [3.3.1.1$^{3,7}$]decane;
4-(5-(1H-indol-5-yl)-pyrimidin-2-yloxy)-1azatricyclo [3.3.1.1$^{3,7}$]decane;
N-(1-azabicyclo[2.2.2]oct-3-yl)-1H-indazole-3-carboxamide;
N-((3R)-1-azabicyclo[2.2.2]oct-3-yl)-1H-indazole-3-carboxamide
N-((3S)-1-azabicyclo[2.2.2]oct-3-yl)-1H-indazole-3-carboxamide
N-(1-azabicyclo[2.2.2]oct-3-yl)-5-(trifluoromethoxy)-1H-indazole-3-carboxamide;
N-((3R)-1-azabicyclo[2.2.2]oct-3-yl)-5-(trifluoromethoxy)-1H-indazole-3-carboxamide;
N-((3S)-1-azabicyclo[2.2.2]oct-3-yl)-5-(trifluoromethoxy)-1H-indazole-3-carboxamide;
N-(2-((3-pyridinyl)methyl)-1-azabicyclo[2.2.2]oct-3-yl) benzofuran-2-carboxamide;
(2S,3R)—N-(2-((3-pyridinyl)methyl)-1-azabicyclo[2.2.2] oct-3-yl)benzofuran-2-carboxamide;
N-(2-((3-pyridinyl)methyl)-1-azabicyclo[2.2.2]oct-3-yl)-3,5-difluorobenzamide; (2S,3R)—N-(2-((3-pyridinyl)methyl)-1-azabicyclo[2.2.2]oct-3-yl)-3,5-difluorobenzamide;
N-(2-((3-pyridinyl)methyl)-1-azabicyclo[2.2.2]oct-3-yl)-5-methylthiophene-2-carboxamide;
(2S,3R)—N-(2-((3-pyridinyl)methyl)-1-azabicyclo[2.2.2] oct-3-yl)-5-methylthiophene-2-carboxamide;
N-(2-((3-pyridinyl)methyl)-1-azabicyclo[2.2.2]oct-3-yl)-5-(2-pyridinyl)thiophene-2-carboxamide;
(2S,3R)—N-(2-((3-pyridinyl)methyl)-1-azabicyclo[2.2.2] oct-3-yl)-5-(2-pyridinyl)thiophene-2-carboxamide;
7,8,9,10-tetrahydro-6,10-methano-6H-pyrazino-(2,3-h)(3)-benzazepine;
3-[1-(2,4-Dimethoxy-phenyl)-meth-(E)-ylidene]-3,4,5,6-tetrahydro-[2,3']bipyridinyl;
N-methyl-1-{5-[3'H-spiro[4-azabicyclo[2.2.2]octane-2,2'-furo[2,3-b]pyridin]-5'-yl]-2-thienyl}methanamine;
N-methyl-1-{5-[(2R)-3'H-spiro[4-azabicyclo[2.2.2]octane-2,2'-furo[2,3-b]pyridin]-5'-yl]-2-thienyl}methanamine;
N-methyl-1-{5-[(2S)-3'H-spiro[4-azabicyclo[2.2.2]octane-2,2'-furo[2,3-b]pyridin]-5'-yl]-2-thienyl}methanamine;
(R)-7-chloro-N-(quinuclidin-3-yl)benzo[b]thiophene-2-carboxamide;
5-{5-[(endo)-8-azabicyclo[3.2.1]octan-3-yloxy]pyridin-2-yl}-1H-indole;
5-{5-[(exo)-8-azabicyclo[3.2.1]octan-3-yloxy]pyridin-2-yl}-1H-indole;
5-{5-[(endo)-8-methyl-8-aza-bicyclo[3.2.1]oct-3-yloxy] pyridin-2-yl}-1H-indole;
5-{5-[(exo)-8-methyl-8-aza-bicyclo[3.2.1]oct-3-yloxy]pyridin-2-yl}-1H-indole;
4-{5-[(exo)-8-methyl-8-aza-bicyclo[3.2.1]oct-3-yloxy]pyridin-2-yl}-1H-indole;
5-{6-[(exo)-8-methyl-8-aza-bicyclo[3.2.1]oct-3-yloxy]pyridin-3-yl}-1H-indole;
(2'R)-spiro-[1-azabicyclo[2.2.2]octane-3,2'(3'H)-furo[2,3-b] pyridine];
1,4-Diaza-bicyclo[3.2.2]nonane-4-carboxylic acid 4-bromophenyl ester; and
5-{6-[1-azabicyclo[2.2.2]oct-3-yloxy]pyridazin-3-yl}-1H-indole;
in free base form or in acid addition salt form.

A further aspect of the invention relates to a method for facilitation of emergence from general anesthesia in a subject treated with an general anesthetic agent which comprises administering to said subject an effective amount of the α7 nAChR agonist of the invention.

A further aspect of the invention relates to the use of the α7 nAChR agonist of the invention for the preparation of a medicament for the facilitation of emergence from general anesthesia.

A further aspect of the invention relates to a pharmaceutical composition comprising the α7 nAChR agonist of the invention for intravenous administration.

Figure 1:
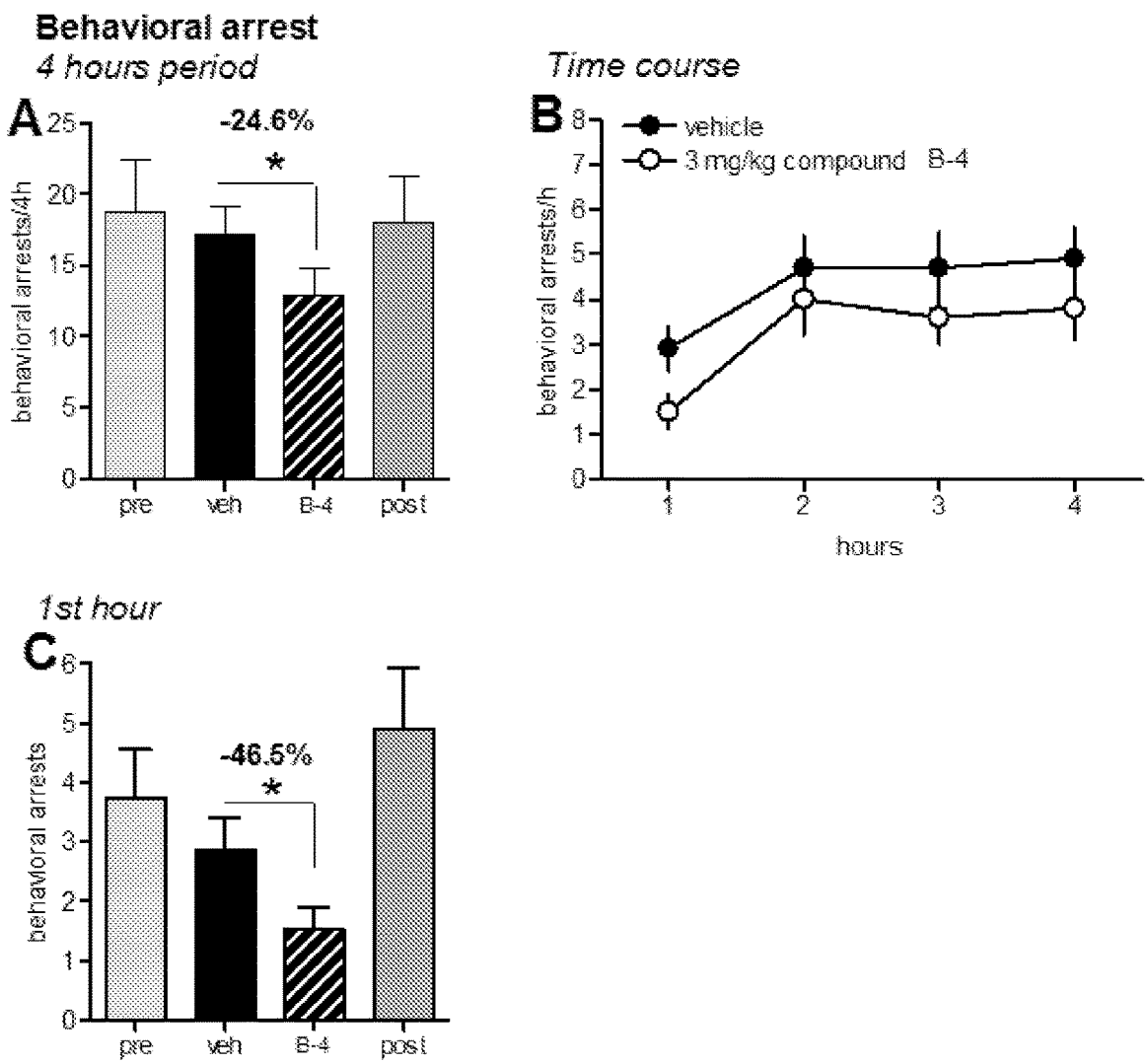
FIG. 1 depicts the effects of 3 mg/kg compound B-4, orally administered directly before lights-off, on the number of narcoleptic episodes (behavioral arrests) in orexin-deficient mice.

It is noted that the drawings are intended to depict only typical aspects of the disclosure, and therefore should not be considered as limiting the scope of the disclosure.

DETAILED DESCRIPTION OF THE INVENTION

As used herein an "α7 nAChR agonist" is a compound that binds to a receptor comprising an α7 nAChR subunit in vivo and in vitro and is activating the receptor. Activation can be measured by the method disclosed in WO2001/85727, i.e. a functional affinity assay at the homomeric α7 nAChR carried out with a rat pituitary cell line stably expressing the α7 nAChR. As read out, the calcium influx upon stimulation of the receptor compared to epibatidine is used. "α7 nAChR agonists of the invention" according to the invention typically induce calcium influx of at least 50% of the maximal influx evoked by epibatidine with an $EC_{50}$ value of at least 1 μM.

In one embodiment, the α7 nAChR agonist of the invention is selective for a receptor comprising a nicotinic acetylcholine receptor alpha 7 subunit, since such an agonist would be expected to cause fewer side effects than a non-selective agonist to a treated subject. An agonist being selective for a receptor comprising a nicotinic acetylcholine receptor alpha 7 subunit has a functional affinity to such a receptor to a much higher degree, e.g. at least 10-fold affinity difference in $EC_{50}$ value, preferably at least 20-fold, more preferably at least 50-fold, compared to any other nicotinic acetylcholine receptor. To assess the affinity of the α7 nAChR agonists of the invention on other nicotinic acetylcholine receptors, the method disclosed in WO2001/85727 can be used, i.e. to assess the affinity on human neuronal α4β2 nAChR, a similar functional assay is carried out using a human embryonic kidney cell line stable expressing the human α4β2 subtype and to assess the activity of the compounds of the invention on the "ganglionic subtype" and the "muscle type" of nicotinic acetylcholine receptor, similar functional assays are carried out with a human embryonic kidney cell line stably expressing the human "ganglionic subtype" or a cell line endogenously expressing the human "muscle type" of nicotinic acetylcholine receptors.

In the last 15 years much effort has been focused on developing selective α7 nAChR agonists leading to the discovery of many different chemotypes displaying said selective activity. These efforts are summarized the review from Horenstein et al (Mol Pharmacol, 2008, 74, 1496-1511, which describes no less than 9 different families of α7 nAChR agonists, in most of which selective agonists have been found. All compounds disclosed in FIG. 1 of said review are incorporated herein by reference. In fact, several drug candidates having an α7 nAChR agonist mode of action entered pre-clinical or even clinical testing (for review: Broad et al, Drugs of the Future, 2007, 32(2), 161-170; Romanelli et al, Expert Opin Ther Patents, 2007, 17(11), 1365-1377). Examples of such compounds—again belonging to a diversity of chemotypes—are MEM3454, MEM63908, SSR180711, GTS21, EVP6124, ABT107 and TC-5619. Further α7 nAChR agonists and their use as pharmaceuticals are known, for example, from WO2001/85727, WO2004/022556, WO2005/118535, WO2005/123732, WO2006/005608, WO2007/045478, WO2007/068476 and WO2007/068475.

The "α7 nAChR agonist of the invention" is
(i) a compound of formula (I)

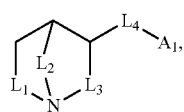

(I)

wherein
$L_1$ is —$CH_2$—; $L_2$ is —$CH_2$—$CH_2$—; and $L_3$ is —$CH_2$— or —$CH(CH_3)$—; or
$L_1$ is —$CH_2$—$CH_2$—; $L_2$ is —$CH_2$—; and $L_3$ is —$CH_2$—$CH_2$—;
$L_4$ is a group selected from

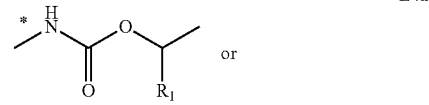

L4a

L4b wherein the bond marked with the asterisk is attached to the azabicycloalkyl moiety;
$R_1$ is methyl;
$X_1$ is —O— or —NH—;
$A_2$ is selected from

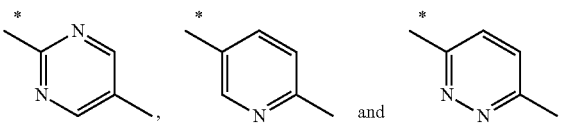

and wherein the bond marked with the asterisk is attached to $X_1$;
$A_1$ is phenyl, indole or 1,3-dihydro-indol-2-one, which may be substituted once or more than once by $R_2$, each $R_2$ independently is $C_{1-6}$alkyl, $C_{1-6}$halogenalkyl or halogen; or (ii) a compound selected from the group consisting of
4-(5-phenyl-1,3,4-thiadiazol-2-yloxy)-1azatricyclo[3.3.1.1$^{3,7}$]decane;
(4S)-4-(5-phenyl-1,3,4-thiadiazol-2-yloxy)-1azatricyclo[3.3.1.1$^{3,7}$]decane;
4-(6-(1H-indol-5-yl)-pyridazin-3-yloxy)-1azatricyclo[3.3.1.1$^{3,7}$]decane;
4-(6-(1H-indol-5-yl)-pyridin-3-yloxy)-1azatricyclo[3.3.1.1$^{3,7}$]decane;
4-(5-(1H-indol-5-yl)-pyrimidin-2-yloxy)-1azatricyclo[3.3.1.1$^{3,7}$]decane;
N-(1-azabicyclo[2.2.2]oct-3-yl)-1H-indazole-3-carboxamide;
N-((3R)-1-azabicyclo[2.2.2]oct-3-yl)-1H-indazole-3-carboxamide
N-((3S)-1-azabicyclo[2.2.2]oct-3-yl)-1H-indazole-3-carboxamide
N-(1-azabicyclo[2.2.2]oct-3-yl)-5-(trifluoromethoxy)-1H-indazole-3-carboxamide;
N-((3R)-1-azabicyclo[2.2.2]oct-3-yl)-5-(trifluoromethoxy)-1H-indazole-3-carboxamide;
N-((3S)-1-azabicyclo[2.2.2]oct-3-yl)-5-(trifluoromethoxy)-1H-indazole-3-carboxamide;
N-(2-((3-pyridinyl)methyl)-1-azabicyclo[2.2.2]oct-3-yl)benzofuran-2-carboxamide;
(2S,3R)—N-(2-((3-pyridinyl)methyl)-1-azabicyclo[2.2.2]oct-3-yl)benzofuran-2-carboxamide;
N-(2-((3-pyridinyl)methyl)-1-azabicyclo[2.2.2]oct-3-yl)-3,5-difluorobenzamide;
(2S,3R)—N-(2-((3-pyridinyl)methyl)-1-azabicyclo[2.2.2]oct-3-yl)-3,5-difluorobenzamide;

N-(2-((3-pyridinyl)methyl)-1-azabicyclo[2.2.2]oct-3-yl)-5-methylthiophene-2-carboxamide;
(2S,3R)—N-(2-((3-pyridinyl)methyl)-1-azabicyclo[2.2.2]oct-3-yl)-5-methylthiophene-2-carboxamide;
N-(2-((3-pyridinyl)methyl)-1-azabicyclo[2.2.2]oct-3-yl)-5-(2-pyridinyl)thiophene-2-carboxamide;
(2S,3R)—N-(2-((3-pyridinyl)methyl)-1-azabicyclo[2.2.2]oct-3-yl)-5-(2-pyridinyl)thiophene-2-carboxamide;
7,8,9,10-tetrahydro-6,10-methano-6H-pyrazino-(2,3-h)(3)-benzazepine;
3-[1-(2,4-Dimethoxy-phenyl)-meth-(E)-ylidene]-3,4,5,6-tetrahydro-[2,3']bipyridinyl;
N-methyl-1-{5-[3'H-spiro[4-azabicyclo[2.2.2]octane-2,2'-furo[2,3-b]pyridin]-5'-yl]-2-thienyl}methanamine;
N-methyl-1-{5-[(2R)-3'H-spiro[4-azabicyclo[2.2.2]octane-2,2'-furo[2,3-b]pyridin]-5'-yl]-2-thienyl}methanamine;
N-methyl-1-{5-[(2S)-3'H-spiro[4-azabicyclo[2.2.2]octane-2,2'-furo[2,3-b]pyridin]-5-yl]-2-thienyl}methanamine;
(R)-7-chloro-N-(quinuclidin-3-yl)benzo[b]thiophene-2-carboxamide;
5-{5-[(endo)-8-azabicyclo[3.2.1]octan-3-yloxy]pyridin-2-yl}-1H-indole;
5-{5-[(exo)-8-azabicyclo[3.2.1]octan-3-yloxy]pyridin-2-yl}-1H-indole;
5-{5-[(endo)-8-methyl-8-aza-bicyclo[3.2.1]oct-3-yloxy]pyridin-2-yl}-1H-indole;
5-{5-[(exo)-8-methyl-8-aza-bicyclo[3.2.1]oct-3-yloxy]pyridin-2-yl}-1H-indole;
4-{5-[(exo)-8-methyl-8-aza-bicyclo[3.2.1]oct-3-yloxy]pyridin-2-yl}-1H-indole;
5-{6-[(exo)-8-methyl-8-aza-bicyclo[3.2.1]oct-3-yloxy]pyridin-3-yl}-1H-indole;
(2'R)-spiro-[1-azabicyclo[2.2.2]octane-3,2'(3'H)-furo[2,3-b]pyridine];
1,4-Diaza-bicyclo[3.2.2]nonane-4-carboxylic acid 4-bromo-phenyl ester; and
5-{6-[1-azabicyclo[2.2.2]oct-3-yloxy]pyridazin-3-yl}-1H-indole;
in free base form or in acid addition salt form.

Unless indicated otherwise, the expressions used in this invention have the following meaning:

"Alkyl" represents a straight-chain or branched-chain alkyl group, for example, methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl.

The alkyl part of "halogenalkyl" and shall have the same meaning as described in the above-mentioned definition of "alkyl", especially regarding linearity and preferential size.

A substituent being substituted "once or more than once", for example as defined for $A_1$, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl; preferably —$CF_3$, —$CHF_2$, —$CH_2F$, —CHF—$CH_3$, —$CF_2CH_3$, or —$CH_2CF_3$.

In the context of the invention, the definition of $A_1$ or $A_3$ as a "five- to ten-membered monocyclic or fused polycyclic aromatic ring system" encompasses a $C_6$- or $C_{10}$-aromatic The acid addition salt forms of the α7 nAChR agonists of the invention are preferably pharmaceutically acceptable salt forms. Such salts are known in the field (e.g. S. M. Berge, et al, "Pharmaceutical Salts", J. Pharm. Sci., 1977, 66:1-19; and "Handbook of Pharmaceutical Salts, Properties, Selection, and Use", Stahl, R H., Wermuth, C. G., Eds.; Wiley-VCH and VHCA: Zurich, 2002). A "pharmaceutically acceptable salt form" is intended to mean a salt form that is not toxic, biologically intolerable, or otherwise biologically undesirable.

On account of asymmetrical carbon atom(s) that may be present in the compounds of formula (I), unless stated otherwise, the compounds may exist in optically active form or in form of mixtures of optical isomers, e.g. in form of racemic mixtures or diastereomeric mixtures. Unless stated otherwise, all optical isomers and their mixtures, including racemic mixtures, are part of the present invention.

In one embodiment, the α7 nAChR agonist of the invention is a compound of formula (I)

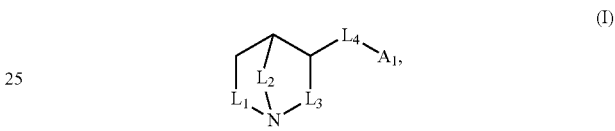

wherein
$L_1$ is —$CH_2$—; $L_2$ is —$CH_2$—$CH_2$—; and $L_3$ is —$CH_2$—;
$L_4$ is L4b;
$A_2$ is selected from

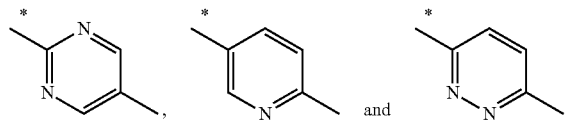

wherein the bond marked with the asterisk is attached to $X_1$;
$A_1$ is phenyl, which may be substituted once or more than once by $R_2$, each $R_2$ independently is $C_{1-6}$alkyl, $C_{1-6}$halogenalkyl or halogen;
in free base form or in acid addition salt form.

In one embodiment, the α7 nAChR agonist of the invention is a compound selected from Group P1 in free base form or in acid addition salt form, wherein Group P1 is the group consisting of
A-1: (S)-(1-aza-bicyclo[2.2.2]oct-3-yl)-carbamic acid (S)-1-(2-fluoro-phenyl)-ethyl ester;
B-1: (R)-3-(6-p-tolyl-pyridin-3-yloxy)-1-aza-bicyclo[2.2.2]octane;
B-2: (R)-3-[6-(2-fluoro-4-methyl-phenyl)-pyridazin-3-yloxy]-1-aza-bicyclo[2.2.2]octane;
B-3: (R)-3-[6-(2,5-difluoro-4-methyl-phenyl)-pyridazin-3-yloxy]-1-aza-bicyclo[2.2.2]octane;
B-4: (2S,3R)-3-[6-(1H-indol-5-yl)-pyridazin-3-yloxy]-2-methyl-1-aza-bicyclo[2.2.2]octane;
C-1: (4S,5R)-4-[5-(1H-indol-5-yl)-pyrimidin-2-yloxy]-1-aza-bicyclo[3.3.1]nonane;
C-2: 5-{2-[(4S,5R)-(1-aza-bicyclo[3.3.1]non-4-yl)oxy]-pyrimidin-5-yl}-1,3-dihydro-indol-2-one;
C-3: (4S,5R)-4-[6-(1H-indol-5-yl)-pyridazin-3-yloxy]-1-aza-bicyclo[3.3.1]nonane;
C-4: 5-{6-[(4S,5R)-(1-aza-bicyclo[3.3.1]non-4-yl)oxy]-pyridazin-3-yl}-1,3-dihydro-indol-2-one; and C-5: (1-aza-bicyclo[3.3.1]non-4-yl)-[5-(1H-indol-5-yl)-pyrimidin-2-yl]-amine.

In one embodiment, the α7 nAChR agonist of the invention is a compound selected from Group P2 in free base form or in acid addition salt form, wherein Group P2 is the group consisting of D-1: 4-(5-phenyl-1,3,4-thiadiazol-2-yloxy)-1azatricyclo[3.3.1.1$^{3,7}$]decane having the formula

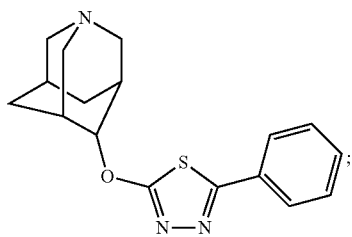 [SMILES: c1ccc(-c2nnc(OC3C4CC5CC3CN(C5)C4)s2)cc1]

D-1a: (4S)-4-(5-phenyl-1,3,4-thiadiazol-2-yloxy)-1azatricyclo[3.3.1.1$^{3,7}$]decane;

D-1b: 4-(6-(1H-indol-5-yl)-pyridazin-3-yloxy)-1azatricyclo[3.3.1.1$^{3,7}$]decane;

D-1c: 4-(6-(1H-indol-5-yl)-pyridin-3-yloxy)-1azatricyclo[3.3.1.1$^{3,7}$]decane;

D-1d: 4-(5-(1H-indol-5-yl)-pyrimidin-2-yloxy)-1azatricyclo[3.3.1.1$^{3,7}$]decane;

D-2: N-(1-azabicyclo[2.2.2]oct-3-yl)-1H-indazole-3-carboxamide;

D-2a: N-((3R)-1-azabicyclo[2.2.2]oct-3-yl)-1H-indazole-3-carboxamide

D-2b: N-((3S)-1-azabicyclo[2.2.2]oct-3-yl)-1H-indazole-3-carboxamide

D-3: N-(1-azabicyclo[2.2.2]oct-3-yl)-5-(trifluoromethoxy)-1H-indazole-3-carboxamide;

D-3a: N-((3R)-1-azabicyclo[2.2.2]oct-3-yl)-5-(trifluoromethoxy)-1H-indazole-3-carboxamide;

D-3b: N-((3S)-1-azabicyclo[2.2.2]oct-3-yl)-5-(trifluoromethoxy)-1H-indazole-3-carboxamide;

D-4: N-(2-((3-pyridinyl)methyl)-1-azabicyclo[2.2.2]oct-3-yl)benzofuran-2-carboxamide;

D-4a: (2S,3R)—N-(2-((3-pyridinyl)methyl)-1-azabicyclo[2.2.2]oct-3-yl)benzofuran-2-carboxamide;

D-5: N-(2-((3-pyridinyl)methyl)-1-azabicyclo[2.2.2]oct-3-yl)-3,5-difluorobenzamide;

D-5a: (2S,3R)—N-(2-((3-pyridinyl)methyl)-1-azabicyclo[2.2.2]oct-3-yl)-3,5-difluorobenzamide;

D-5b: N-(2-((3-pyridinyl)methyl)-1-azabicyclo[2.2.2]oct-3-yl)-5-methylthiophene-2-carboxamide;

D-5c: (2S,3R)—N-(2-((3-pyridinyl)methyl)-1-azabicyclo[2.2.2]oct-3-yl)-5-methylthiophene-2-carboxamide;

D-5d: N-(2-((3-pyridinyl)methyl)-1-azabicyclo[2.2.2]oct-3-yl)-5-(2-pyridinyl)thiophene-2-carboxamide;

D-5e: (2S,3R)—N-(2-((3-pyridinyl)methyl)-1-azabicyclo[2.2.2]oct-3-yl)-5-(2-pyridinyl)thiophene-2-carboxamide;

D-6: 7,8,9,10-tetrahydro-6,10-methano-6H-pyrazino-(2,3-h)(3)-benzazepine;

D-7: 3-[1-(2,4-Dimethoxy-phenyl)-meth-(E)-ylidene]-3,4,5,6-tetrahydro-[2,3']bipyridinyl;

D-8: N-methyl-1-{5-[3'H-spiro[4-azabicyclo[2.2.2]octane-2,2'-furo[2,3-b]pyridin]-5'-yl]-2-thienyl}methanamine having the formula

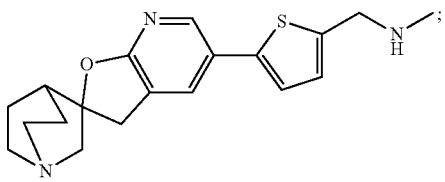 [SMILES: CNCc1ccc(-c2cnc3c(c2)CC2(CN4CCC2CC4)O3)s1]

D-8a: N-methyl-1-{5-[(2R)-3'H-spiro[4-azabicyclo[2.2.2]octane-2,2'-furo[2,3-b]pyridin]-5'-yl]-2-thienyl}methanamine;

D-8b: N-methyl-1-{5-[(2S)-3'H-spiro[4-azabicyclo[2.2.2]octane-2,2'-furo[2,3-b]pyridin]-5'-yl]-2-thienyl}methanamine;

D-9: (R)-7-chloro-N-(quinuclidin-3-yl)benzo[b]thiophene-2-carboxamide;

D-10a: 5-{5-[(endo)-8-azabicyclo[3.2.1]octan-3-yloxy]pyridin-2-yl}-1H-indole;

D-10b: 5-{5-[(exo)-8-azabicyclo[3.2.1]octan-3-yloxy]pyridin-2-yl}-1H-indole;

D-10c: 5-{5-[(endo)-8-methyl-8-aza-bicyclo[3.2.1]oct-3-yloxy]pyridin-2-yl}-1H-indole;

D-10d: 5-{5-[(exo)-8-methyl-8-aza-bicyclo[3.2.1]oct-3-yloxy]pyridin-2-yl}-1H-indole;

D-10e: 4-{5-[(exo)-8-methyl-8-aza-bicyclo[3.2.1]oct-3-yloxy]pyridin-2-yl}-1H-indole;

D-10f: 5-{6-[(exo)-8-methyl-8-aza-bicyclo[3.2.1]oct-3-yloxy]pyridin-3-yl}-1H-indole;

D-11: (2'R)-spiro-[1-azabicyclo[2.2.2]octane-3,2'(3'H)-furo[2,3-b]pyridine];

D-12: 1,4-Diaza-bicyclo[3.2.2]nonane-4-carboxylic acid 4-bromo-phenyl ester; and D-13: 5-{6-[1-azabicyclo[2.2.2]oct-3-yloxy]pyridazin-3-yl}-1H-indole.

In one embodiment, the α7 nAChR agonist of the invention is compound A-1 in free base form or in acid addition salt form.

In one embodiment, the α7 nAChR agonist of the invention is a compound selected from the group consisting of compound B-1, B-2, B-3 and B-4; wherein each of said compound is in free base form or in acid addition salt form.

In one embodiment, the α7 nAChR agonist of the invention is a compound B-1 in free base form or in acid addition salt form. In another embodiment, the α7-nAChR agonist of the invention is compound B-1, which is in fumarate salt form. In yet another embodiment, the α7-nAChR agonist of the invention is the mono-fumarate salt of compound B-1.

In one embodiment, the α7 nAChR agonist of the invention is a compound B-4 in free base form or in acid addition salt form.

In one embodiment, the α7 nAChR agonist of the invention is a compound selected from the group consisting of compound C-1, C-2, C-3, C-4 and C-5; wherein each of said compound is in free base form or in acid addition salt form.

In one embodiment, the α7 nAChR agonist of the invention is a compound C-3 in free base form or in acid addition salt form.

In one embodiment, the α7 nAChR agonist of the invention is a compound C-4 in free base form or in acid addition salt form.

In one embodiment, the α7 nAChR agonist of the invention is a compound C-5 in free base form or in acid addition salt form.

In one embodiment, the α7 nAChR agonist of the invention is a compound selected from the group consisting of compound D-1, D-1a, D-1b, D-1c, D-1d, D-4, D-4a and D-9; wherein each of said compound is in free base form or in acid addition salt form.

In one embodiment, the α7 nAChR agonist of the invention is a compound selected from Group P3; Group P3 is the group consisting of compounds A-1, B-1, B-2, B-3, B-4, C-1, C-2, C-3, C-4, C-5, D-1, D-1a, D-1b, D-1c, D-1d, D-4, D-4a and D-9; wherein each of said compound is in free base form or in acid addition salt form.

The compounds of formula (I) (e.g. compounds A-1, B-1 to B-4 and C-1 to C-5) and their manufacture are known from WO2001/85727, WO2004/022556, WO2005/123732, WO2006/005608, WO2007/045478, WO2007/068476 and WO2007/068475, or can be prepared analogously to said references.

Compounds D-1 and D-1 a can be prepared according to WO2008/058096.

Compounds D-2, D-2a, D-2b, D-3, D-3a and D-3b can be prepared according to WO2004/029050 and/or WO2010/043515.

Compounds D-4 and D-4a can be prepared according to WO2004/076449 and/or WO2009/018505;

Compounds D-5, D-5a to D-5e can be prepared according to WO2004/076449 and/or WO2010/085724 and/or WO2010/056622;

Compound D-6 (varenicline) is described in O'Donnell et al, J Med Chem, 2010, 53, 1222-1237.

Compound D-7 (GTS-21) is described in Haydar et al, Current Topics in Medicinal Chemistry, 2010, 10, 144-152.

Compound D-8, D-8a and D-8b are described in WO2007/133155 and/or WO2009/066107.

Compound D-9 is described in WO2003/055878.

Compounds D-10a to D-10f are described in WO2007/137030.

Compound D-11 (AZD-0328) is described in Haydar et al, Current Topics in Medicinal Chemistry, 2010, 10, 144-152.

Compound D-12 (SSR-190771) is described Horenstein et al, Mol Pharmacol, 2008, 74, 1496-1511.

Compound D-13 (ABT-107) can be prepared according to WO2006/065233 and/or WO2007/018738.

Facilitation of Emergence from General Anesthesia:

General anesthesia can be regarded as a reversible loss of consciousness actively induced and maintained by treatment of patients with general anesthetics.

General anesthetics, when administered to subjects, cause general anesthesia. General anesthetics include intravenous anesthetics and inhalation anesthetics (gas anesthetics).

Intravenous anesthetics, once injected, quickly reach the brain and cause loss of consciousness. Intravenous anesthetics are divided into short-acting and long-acting anesthetics. Widely used intravenous anesthetics are propofol; etomidate; barbiturates (e.g. methohexital, thiamylal and thiopental); benzodiazepines (e.g. midazolam); and ketamine. Propofol is one of the most commonly used intravenous anesthetics employed to induce and maintain general anesthesia.

Inhalation anesthetics are generally volatile and have the advantage of being absorbed and discarded by the lungs. Said anesthetics are usually delivered using an anesthesia machine. Such a machine allows the user to (i) mix inhalation anesthetics, oxygen and ambient air; (ii) administer said mixture to the patient and (iii) monitor patient and machine parameters. Liquid inhalation anesthetics are vaporized in the machine. Widely used inhalation anesthetics are e.g. halogenated ethers (e.g. desflurane, isoflurane, sevoflurane, enflurane and/or methoxyflurane) which are often combined with nitrous oxide; halothane; and xenon. Inhalation anesthetics have a common characteristic of typically prompt induction of and emergence from general anesthesia. However, inhalation anesthetics have respiratory and cardiovascular side effects and may lead to coughing and laryngospasm.

Although it is possible to induce and maintain general anesthesia solely by intravenous anesthetics or inhalation anesthetics, most commonly intravenous anesthetics and inhalation anesthetics are used in combination. Typically, an intravenous anesthetic is administered to induce general anesthesia and an inhalation anesthetic is administered for maintenance.

The term "general anesthetic agent" as used herein refers to the agent causing general anesthesia in the subject to which the method of facilitation of emergence from general anesthesia is applied. Said general anesthetic agent may be a single general anesthetic or a plurality of different general anesthetics, e.g. two general anesthetics. In case of a plurality of different general anesthetics, the different general anesthetics may be used in different periods of general anesthesia, e.g. one general anesthetic for the induction period and another general anesthetic for the maintenance period.

In one embodiment, the invention relates to facilitation of emergence from general anesthesia in a subject treated with a general anesthetic agent.

In one embodiment, the general anesthetic agent is selected from an intravenous anesthetic and an inhalation anesthetic, or a combination thereof.

In one embodiment, the general anesthetic agent is selected from propofol; etomidate; a barbiturate; a benzodiazepine; ketamine, a halogenated ether, alone or combined with nitrous oxide; halothane; and xenon; or a combination thereof.

In one embodiment, the general anesthetic agent is a combination of ketamine for the induction period and sevoflurane for the maintenance period.

In general anesthesia, commonly further drugs are used. One example is a muscle relaxant, e.g. rocuronium, which facilitate intubation and/or surgery by paralyzing the skeletal muscle. Another example is an opioid which is used as analgesic agent. Opioids can be used to relieve pain of patients before, during or after surgery. The following opioids are frequently used during general anesthesia: alfentanil, fentanyl, remifentanil and sufentanil.

During general anesthesia, arousal of the subject is not possible, the subject is unconscious and unresponsive. Furthermore, the subject is commonly under apnea and ventilation of the subject is mechanically controlled (normally by intubation). Subjects under general anesthesia must undergo continuous physiological monitoring to ensure safety. Typical monitored parameters are electrocardiography (ECG), heart rate, blood pressure, inspired and expired gases, oxygen saturation of the blood (pulse oximetry) and temperature.

"Emergence from general anesthesia" occurs after cessation of administration of the general anesthetic agent at doses causing general anesthesia. Emergence from general anesthesia is characterized by restoration of consciousness in the subject, restoration of ability to answer simple questions, restoration of mobility, and restoration of ability to maintain adequate ventilation/protect airways. First signs of awakening typically are the transition of the subject from apnea or machine-controlled breathing to irregular breathing and then to regular breathing. Emergence from general anesthesia may be associated with complications, e.g. anesthesia-caused delirium and/or POCD. Both complications may continue after emergence from anesthesia.

"Anesthesia-caused delirium" may be emergence delirium or hypoactive emergence delirium which are described in Radtke et al (Minerva Anestiol 2010, 76(6), 394-403). Delirium is disturbance of consciousness and a change in cognition or a perception of mental dissociation that can include hallucinations, psychomotor agitation and delusions, and can include restlessness, incoherence, irritability, screaming and involuntary activity, as well as belligerent behaviours and disorientation. Delirium can be quantitated using the Ryker sedation-agitated scale (Lepouse et al, J Anesthesia, 2006, 96, 747-753), and includes assessment of eye contact, purposeful actions, awareness of surroundings, restlessness and inconsolability and the like. Emergence delirium may also referred to as emergence agitation which is a phenomenon occurring in children and adults in the immediate postoperative period. In children, emergence delirium is defined as a dissociated state of consciousness in which the child is inconsolable, irritable, uncompromising or uncooperative, typically trashing, crying, moaning or incoherent. Although generally self limiting (5-15 minutes), emergence delirium can be severe and may result in physical harm to the child and particularly the site of surgery.

Signs and symptoms of anesthesia-caused delirium include excitement and alternating periods of lethargy followed by excitement and disorientation. Inappropriate behavior such as screaming and kicking and use of profanities may also occur. Also, the patients may not respond appropriately to commands. Anesthesia-caused delirium has the risk of injury to patient and/or hospital staff.

Emergence delirium can occur after most inhalational agents, e.g. desflurane and sevoflurane, and intravenous agents, e.g. midazolam, remifentanil and propofol.

Physiological causes of emergence delirium include age, hypoxemia, hypercapnia, hyponatremia, hypoglycemia, intracranial injury, sepsis, alcohol withdrawal, airway obstruction, gastric dilatation, full bladder, pain, hypothermia, sensory overload, sensory deprivation and electrolyte disturbances. Pharmacological causes of emergence delirium include rapid emergence, ketamine, droperidol, benzodiazepines, metoclopramide, atropine, scopolamine, volatile anesthetics, central anticholinergic syndrome, neuroleptics, digoxin, beta-blockers, steroids, anticonvulsants and oral hypoglycemic.

Risk factors for emergence delirium are known, e.g. age (e.g. ages 2-5 are most vulnerable), underlying medical condition, medication, CNS disorders, electrolyte disturbances, temperament, surgery type and anesthesia type.

Postoperative Cognitive Dysfunction (POCD) relates to a decline in cognitive function, typically for weeks or months after surgery. Within the first week after surgery, 30-50% of patients have POCD, with no difference by age. At 3 months after surgery about 10-15% of patients have POCD, but at this time point, POCD is basically limited to the elderly (G Crosby and D J Culley, Anesthesia and Analgesia, 2011, 112(5), 999-1001). POCD is common after cardiac surgery; also exists after major non-cardiac surgery—although at a lower incidence (L S Rasmussen, Best practice & research in clinical anaesthesiology, 2006, 20(2), 315-330). Patients with POCD are at an increased risk of death in the first year after surgery. The relevance of POCD is increasing, especially as more elderly patients are able to undergo successful minor and major surgeries.

The term "subject" as used herein refers to a human being, especially to a patient, e.g. a perioperative patient.

In one embodiment, the subject is a perioperative patient under general anesthesia.

The term "facilitation of emergence from general anesthesia" as used herein refers to improving the speed and/or the quality of emergence from general anesthesia.

The term "effective amount" as used herein typically refers to an α7 nAChR agonist of the invention amount which, when administered to a subject, is sufficient to provide facilitation of emergence from general anesthesia, i.e. is sufficient to measurably facilitate emergence of a subject from general anesthesia-induced unconsciousness; e.g. cause a measurable decrease in time to regain consciousness as compared to in the absence of the α7 nAChR agonist of the invention; and/or decreases anesthesia-caused delirium, and/or decreases the time period until the subject is able to answer simple questions.

Effective amounts will vary depending e.g. on the severity, duration and type of anesthesia; the medical condition of the subject; on the nature and/or duration of the surgery and the age and/or physical condition of the subject.

Effective amounts can further be detected by physiological effects, e.g. transition from apnea to irregular breathing or to regular breathing, time to righting (e.g. righting responses); time to emergence from anesthesia-induced unconsciousness; monitoring changes in electroencephalograms (e.g. when the subject shifts from low frequencies to higher frequencies in EEG power spectrum, the latter being the dominat pattern seen in the awakening state). Relevant assays to measure such effects include electroencephalogram, observation, spectrograms, arterial blood gas and hemodynamic recordings, measurements of respiratory rate, mean arterial blood pressure and heart rate.

One aspect of the facilitation of emergence from general anesthesia is that said facilitation should have a minimal adverse effect on the patient. For example, facilitation may disturb nocturnal sleep in many patients. Highly relevant would be e.g. an agent that can be used to facilitate emergence from general anesthesia while producing only little or substantially no side effects. Further highly relevant for the facilitation of emergence from general anesthesia in elderly would be an agent that has a positive effect on POCD which may occur e.g. in elderly patients.

Agents facilitating emergence from general anesthesia preferably shorten the period to full cognitive function after general anesthesia-induced unconsciousness and substantially do not affect the effectiveness of the surgery, post-surgery recovery period or long term cognitive function of the subject.

The α7 nAChR agonist of the invention is typically administered to the subject after administration of the general anesthetic agent.

In some embodiments, when the α7 nAChR agonist of the invention is administered, the subject is no longer being treated with the general anesthetic agent. In some of said embodiments, the α7 nAChR agonist of the invention is administered to the subject immediately upon cessation of administration of the general anesthetic agent, such that as soon as the general anesthetic agent is stopped being administered, the α7 nAChR agonist of the invention is administered to the subject.

In alternative embodiments, the α7 nAChR agonist of the invention is administered to the subject prior to cessation of treatment with the general anesthetic agent, e.g. immediately prior and/or in the last 10% of the surgery. In such embodiments, the dose of the general anesthetic agent can be reduced with an inverse relationship to the increasing dose of the α7 nAChR agonist of the invention, so that, for example, the dose of the general anesthetic agent is reduced concurrently with an increase in the dose of the α7 nAChR agonist of the invention.

In some embodiments, the methods for emerging a subject from general anesthesia further comprises administering to the subject at least one other therapeutic agent with the α7 nAChR agonist of the invention, wherein the other therapeutic agent can be selected from the group consisting of an analgesic, pain medication and anti-inflammatory agent.

Furthermore, an α7 nAChR agonist of the invention may be administered to a subject suffering from one or more symptoms of the anesthesia-caused delirium upon awakening. Furthermore, an α7 nAChR agonist of the invention can also be administered to an unconscious subject who is inadvertently or accidentally oversedated with an general anesthetic agent.

Administration/Dosing:

In one embodiment, the α7 nAChR agonist of the invention is administered by intravenous or intra-arterial administration.

In one embodiment, the α7 nAChR agonist of the invention is administered by intravenous administration.

In one embodiment, the α7 nAChR agonist of the invention is administered by intravenous administration when the subject is no longer being treated with a general anesthetic agent.

In one embodiment, the α7 nAChR agonist of the invention is administered to a subject by intravenous administration, immediately after or just before stopping the administration of the general anesthetic agent.

In one embodiment, the α7 nAChR agonist of the invention is administered by intravenous administration continuously, e.g. over the whole period the subject is regaining consciousness.

In one embodiment, the α7 nAChR agonist of the invention is administered by continuous intravenous infusion.

In one embodiment, the continuous intravenous infusion is by an infusion pump or by gravity drip. An infusion pump allows precise control over the flow rate and total amount delivered. However, in cases where a change in the flow rate would not have serious consequences, or if pumps are not available, the drip is often left to flow simply by placing the bag above the level of the patient and using the clamp to regulate the rate; this is the so-called "gravity drip".

In one embodiment, the continuous intravenous infusion is by a rapid infuser. A rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused.

In one embodiment, the α7 nAChR agonist of the invention is administered by multiple, e.g. two or more than two, continuous intravenous infusions which are separated by times of no infusion of the α7 nAChR agonist of the invention.

In one embodiment, the α7 nAChR agonist of the invention is administered by intermittent intravenous infusion.

Intermittent infusion is used when a patient requires medications only at certain times, and does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, a "flush", following the injection to push the medicine into the bloodstream more quickly.

In one embodiment, the α7 nAChR agonist of the invention is administered by bolus injection. The α7 nAChR agonist of the invention may be administered as a bolus injection immediately after surgery and then injected sequentially over time (episodically), e.g. every hour, until the subject regained consciousness.

For the above-mentioned facilitation method the appropriate dosage will vary depending upon, for example, the compound employed, the host and the nature and severity of the anesthesia for which emergence is facilitated.

The term "daily dosage" as used herein, unless stated otherwise, refers to the dosage of the α7 nAChR agonist of the invention administered to a subject within 24 hours.

For example, in animals a daily dosage of an α7 nAChR agonist of the invention from 1 to 100 mg/kg body weight may be used, e.g. from 1 to 50 mg/kg body weight, e.g. about 10 mg/kg. In larger mammals, for example humans, an indicated daily dosage may be in the range from 0.5 to 500 mg, e.g. from 1 to 200 mg, e.g. from 10 to 100 mg, e.g. about 75 mg of an α7 nAChR agonist of the invention.

In one embodiment, the α7 nAChR agonist of the invention is administered by continuous intravenous infusion within 5 to 60 minutes, e.g. 10 to 60 minutes.

In one embodiment, the α7 nAChR agonist of the invention is administered by continuous intravenous infusion within 10 to 30 minutes, e.g. 10 to 20 minutes.

In one embodiment, the α7 nAChR agonist of the invention is administered by continuous intravenous infusion lasting at least 5 minutes.

In one embodiment, the α7 nAChR agonist of the invention is administered by continuous intravenous infusion lasting maximal 60 minutes.

In one embodiment, the α7 nAChR agonist of the invention is administered at a dose of 1 to 200 mg by continuous intravenous infusion within 10 to 60 minutes.

In one embodiment, the α7 nAChR agonist of the invention is administered at a dose of 10 to 100 mg by continuous intravenous infusion within 10 to 20 minutes.

In one embodiment, the α7 nAChR agonist of the invention is administered at a dose of about 75 mg by continuous intravenous infusion within 10 to 60 minutes.

In one embodiment, the α7 nAChR agonist of the invention is administered at a dose of about 75 mg by continuous intravenous infusion within 10 to 20 minutes.

Patients may continue to receive an α7 nAChR agonist of the invention even after emergence has occurred, this may be particularly relevant for subjects facing/being at risk for POCD. In such situations, the α7 nAChR agonist of the invention may be administered for facilitation of emergence from general anesthesia by intravenous administration and after emergence by the same or another route of administration, e.g. by oral administration.

Pharmaceutical Compositions:

The present invention provides a pharmaceutical composition for the facilitation of emergence from general anesthesia comprising an α7 nAChR agonist of the invention and at least one pharmaceutically acceptable excipient.

Such compositions may be manufactured in conventional manner. Unit dosage forms may contain, for example, from about 0.5 to about 50 mg, e.g. from about 2.5 to about 25 mg, of one or more of the α7 nAChR agonists of the invention.

For use according to the invention, the α7 nAChR agonist of the invention may be administered as single active agent or in combination with other active agents.

In one embodiment, the administration of the composition comprising an α7 nAChR agonist of the invention is carried out in single or multiple doses.

In one embodiment, the composition comprising an α7 nAChR agonist of the invention is administered intravenously in an effective dosage.

The dose of the active ingredient depends on the species of warm-blooded animal, body weight, age and individual condition and individual pharmacokinetic data.

The pharmaceutical compositions are preferably in the form of an aqueous solution, for example, in unit dose form. Such compositions are preferably contained in ampoules or vials.

The pharmaceutical compositions of the present invention are prepared according to standard process for sterile products comprising the steps of compounding, dissolution, pH-adjustment, mixing, filtration, filling and antimicrobial treatment.

The present invention provides a pharmaceutical composition for intravenous administration comprising an alpha 7 nicotinic acetylcholine receptor agonist of the invention; and at least one pharmaceutically acceptable excipient.

In one embodiment, said composition is in the form of an aqueous solution.

In one embodiment, said composition comprises from 0.5 to 50 mg, e.g. from 2.5 to 25 mg, of the alpha 7 nicotinic acetylcholine receptor agonist of the invention.

In one embodiment, said composition comprises (R)-3-(6-p-tolyl-pyridin-3-yloxy)-1-aza-bicyclo[2.2.2]octane in free base form or in acid addition salt form as alpha 7 nicotinic acetylcholine receptor agonist of the invention.

The present invention provides a pharmaceutical composition in the form of an aqueous solution for intravenous administration comprising from 0.5 to 50 mg of (R)-3-(6-p-tolyl-pyridin-3-yloxy)-1-aza-bicyclo[2.2.2]octane in free base form or in acid addition salt form; and at least one pharmaceutically acceptable excipient.

The present invention provides a pharmaceutical composition in the form of an aqueous solution for intravenous administration comprising from 0.5 to 50 mg of (R)-3-(6-p-tolyl-pyridin-3-yloxy)-1-aza-bicyclo[2.2.2]octane in free base form or in acid addition salt form; and sodium chloride.

The present invention provides a pharmaceutical composition in the form of an aqueous solution for intravenous administration comprising from 0.5 to 50 mg of (R)-3-(6-p-tolyl-pyridin-3-yloxy)-1-aza-bicyclo[2.2.2]octane in free base form or in acid addition salt form;

sodium chloride; and a pH adjustment agent.

In one embodiment, the pH adjustment agent is sodium hydroxide.

In one embodiment, the pH adjustment agent is hydrochloric acid.

Further Embodiments of the Invention:

Embodiment 1-1: An α7 nAChR agonist of the invention for use in the facilitation of emergence from general anesthesia; wherein said α7 nAChR agonist is a compound selected from Group P1 in free base form or in acid addition salt form.

Embodiment 1-2. An α7 nAChR agonist according to embodiment 1-1 for use in the facilitation of emergence from general anesthesia in a subject treated with a general anesthetic agent.

Embodiment 1-3. An α7 nAChR agonist according to embodiment 1-2, wherein the general anesthetic agent is selected from an intravenous anesthetic and an inhalation anesthetic, or a combination thereof.

Embodiment 1-4. An α7 nAChR agonist according to embodiment 1-2, wherein the general anesthetic agent is selected from propofol; etomidate; a barbiturate; a benzodiazepine; ketamine, a halogenated ether, alone or combined with nitrous oxide; halothane; and xenon; or a combination thereof.

Embodiment 1-5. An α7 nAChR agonist according to embodiment 1-2, wherein the general anesthetic agent is a combination of ketamine for the induction period and sevoflurane for the maintenance period.

Embodiment 1-6. An α7 nAChR agonist according to embodiment 1-2, wherein the subject is a perioperative patient.

Embodiment 1-7. An α7 nAChR agonist according to embodiment 1-2, wherein the agonist is administered by intravenous administration.

Embodiment 1-8. An α7 nAChR agonist according to embodiment 1-2, wherein the agonist is administered by intravenous administration when the subject is no longer being treated with the general anesthetic agent.

Embodiment 1-9. An α7 nAChR agonist according to embodiment 1-7, wherein the administration is continuous intravenous infusion within 10 to 60 minutes.

Embodiment 1-10. An α7 nAChR agonist according to embodiment 1-7, wherein the administration is continuous intravenous infusion within 10 to 20 minutes.

Embodiment 1-11. An α7 nAChR agonist according to embodiment 1-7, wherein the daily dosage of the agonist is from 1 to 200 mg.

Embodiment 1-12. An α7 nAChR agonist according to embodiment 1-7, wherein the daily dosage of the agonist is from 10 to 100 mg.

Embodiment 1-13. An α7 nAChR agonist according to embodiment 1-7, wherein the administration is continuous intravenous infusion of 1 to 200 mg of the agonist within 10 to 60 minutes.

Embodiment 1-14. An α7 nAChR agonist according to embodiment 1-1 for use in the facilitation of emergence from general anesthesia in a subject treated with a general anesthetic agent;

wherein the general anesthetic agent is selected from propofol; etomidate; a barbiturate; a benzodiazepine; ketamine, a halogenated ether, alone or combined with nitrous oxide; halothane; and xenon; or a combination thereof;

wherein the subject is a perioperative patient; and wherein the administration is continuous intravenous infusion within 10 to 60 minutes.

Embodiment 2-1: An α7 nAChR agonist of the invention for use in the facilitation of emergence from general anesthesia; wherein said α7 nAChR agonist is a compound selected from Group P2 in free base form or in acid addition salt form.

Embodiment 2-2. An α7 nAChR agonist according to embodiment 2-1 for use in the facilitation of emergence from general anesthesia in a subject treated with a general anesthetic agent.

Embodiment 2-3. An α7 nAChR agonist according to embodiment 2-2, wherein the general anesthetic agent is selected from an intravenous anesthetic and an inhalation anesthetic, or a combination thereof.

Embodiment 2-4. An α7 nAChR agonist according to embodiment 2-2, wherein the general anesthetic agent is selected from propofol; etomidate; a barbiturate; a benzodiazepine; ketamine, a halogenated ether, alone or combined with nitrous oxide; halothane; and xenon; or a combination thereof.

Embodiment 2-5. An α7 nAChR agonist according to embodiment 2-2, wherein the general anesthetic agent is a combination of ketamine for the induction period and sevoflurane for the maintenance period.

Embodiment 2-6. An α7 nAChR agonist according to embodiment 2-2, wherein the subject is a perioperative patient.

Embodiment 2-7. An α7 nAChR agonist according to embodiment 2-2, wherein the agonist is administered by intravenous administration.

Embodiment 2-8. An α7 nAChR agonist according to embodiment 2-2, wherein the agonist is administered by intravenous administration when the subject is no longer being treated with the general anesthetic agent.

Embodiment 2-9. An α7 nAChR agonist according to embodiment 2-7, wherein the administration is continuous intravenous infusion within 10 to 60 minutes.

Embodiment 2-10. An α7 nAChR agonist according to embodiment 2-7, wherein the administration is continuous intravenous infusion within 10 to 20 minutes.

Embodiment 2-11. An α7 nAChR agonist according to embodiment 2-7, wherein the daily dosage of the agonist is from 1 to 200 mg.

Embodiment 2-12. An α7 nAChR agonist according to embodiment 2-7, wherein the daily dosage of the agonist is from 10 to 100 mg.

Embodiment 2-13. An α7 nAChR agonist according to embodiment 2-7, wherein the administration is continuous intravenous infusion of 1 to 200 mg of the agonist within 10 to 60 minutes.

Embodiment 2-14. An α7 nAChR agonist according to embodiment 2-1 for use in the facilitation of emergence from general anesthesia in a subject treated with a general anesthetic agent;
wherein the general anesthetic agent is selected from propofol; etomidate; a barbiturate; a benzodiazepine; ketamine, a halogenated ether, alone or combined with nitrous oxide; halothane; and xenon; or a combination thereof;
wherein the subject is a perioperative patient; and
wherein the administration is continuous intravenous infusion within 10 to 60 minutes.

Embodiment 3-1. An α7 nAChR agonist of the invention for use in the facilitation of emergence from general anesthesia; wherein said α7 nAChR agonist is a compound selected from Group P3 in free base form or in acid addition salt form.

Embodiment 3-2. An α7 nAChR agonist according to embodiment 3-1 for use in the facilitation of emergence from general anesthesia in a subject treated with a general anesthetic agent.

Embodiment 3-3. An α7 nAChR agonist according to embodiment 3-2, wherein the general anesthetic agent is selected from an intravenous anesthetic and an inhalation anesthetic, or a combination thereof.

Embodiment 3-4. An α7 nAChR agonist according to embodiment 3-2, wherein the general anesthetic agent is selected from propofol; etomidate; a barbiturate; a benzodiazepine; ketamine, a halogenated ether, alone or combined with nitrous oxide; halothane; and xenon; or a combination thereof.

Embodiment 3-5. An α7 nAChR agonist according to embodiment 3-2, wherein the general anesthetic agent is a combination of ketamine for the induction period and sevoflurane for the maintenance period.

Embodiment 3-6. An α7 nAChR agonist according to embodiment 3-2, wherein the subject is a perioperative patient.

Embodiment 3-7. An α7 nAChR agonist according to embodiment 3-2, wherein the agonist is administered by intravenous administration.

Embodiment 3-8. An α7 nAChR agonist according to embodiment 3-2, wherein the agonist is administered by intravenous administration when the subject is no longer being treated with the general anesthetic agent.

Embodiment 3-9. An α7 nAChR agonist according to embodiment 3-7, wherein the administration is continuous intravenous infusion within 10 to 60 minutes.

Embodiment 3-10. An α7 nAChR agonist according to embodiment 3-7, wherein the administration is continuous intravenous infusion within 10 to 20 minutes.

Embodiment 3-11. An α7 nAChR agonist according to embodiment 3-7, wherein the daily dosage of the agonist is from 1 to 200 mg.

Embodiment 3-12. An α7 nAChR agonist according to embodiment 3-7, wherein the daily dosage of the agonist is from 10 to 100 mg.

Embodiment 3-13. An α7 nAChR agonist according to embodiment 3-7, wherein the administration is continuous intravenous infusion of 1 to 200 mg of the agonist within 10 to 60 minutes.

Embodiment 3-14. An α7 nAChR agonist according to embodiment 3-1 for use in the facilitation of emergence from general anesthesia in a subject treated with a general anesthetic agent;
wherein the general anesthetic agent is selected from propofol; etomidate; a barbiturate; a benzodiazepine; ketamine, a halogenated ether, alone or combined with nitrous oxide; halothane; and xenon; or a combination thereof;
wherein the subject is a perioperative patient; and
wherein the administration is continuous intravenous infusion within 10 to 60 minutes.

Further Emobidments of the Invention:

Embodiment 1: An alpha 7 nicotinic acetylcholine receptor agonist for use in the facilitation of emergence from general anesthesia;
wherein said alpha 7 nicotinic acetylcholine receptor agonist is
(i) a compound of formula (I)

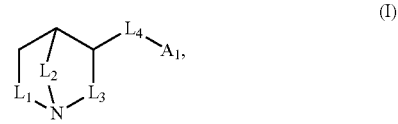

wherein
$L_1$ is —$CH_2$—; $L_2$ is —$CH_2$—$CH_2$—; and $L_3$ is —$CH_2$— or —$CH(CH_3)$—; or
$L_1$ is —$CH_2$—$CH_2$—; $L_2$ is —$CH_2$—; and $L_3$ is —$CH_2$—$CH_2$—;

L4 is a group selected from

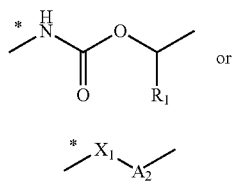

wherein the bond marked with the asterisk is attached to the azabicycloalkyl moiety;
$R_1$ is methyl;
$X_1$ is —O— or —NH—;
$A_2$ is selected from

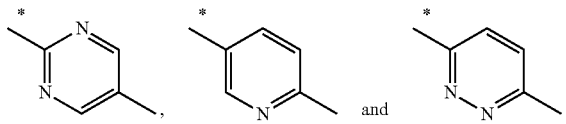

wherein the bond marked with the asterisk is attached to $X_1$;
$A_1$ is phenyl, indole or 1,3-dihydro-indol-2-one, which may be substituted once or more than once by $R_2$, each $R_2$ independently is $C_{1-6}$alkyl, $C_{1-6}$halogenalkyl or halogen; or (ii) a compound selected from the group consisting of
4-(5-phenyl-1,3,4-thiadiazol-2-yloxy)-1azatricyclo[3.3.1.1$^{3,7}$]decane;
(4S)-4-(5-phenyl-1,3,4-thiadiazol-2-yloxy)-1azatricyclo[3.3.1.1$^{3,7}$]decane;
4-(6-(1H-indol-5-yl)-pyridazin-3-yloxy)-1azatricyclo[3.3.1.1$^{3,7}$]decane;
4-(6-(1H-indol-5-yl)-pyridin-3-yloxy)-1azatricyclo[3.3.1.1$^{3,7}$]decane;
4-(5-(1H-indol-5-yl)-pyrimidin-2-yloxy)-1azatricyclo[3.3.1.1$^{3,7}$]decane;
N-(1-azabicyclo[2.2.2]oct-3-yl)-1H-indazole-3-carboxamide;
N-((3R)-1-azabicyclo[2.2.2]oct-3-yl)-1H-indazole-3-carboxamide
N-((3S)-1-azabicyclo[2.2.2]oct-3-yl)-1H-indazole-3-carboxamide
N-(1-azabicyclo[2.2.2]oct-3-yl)-5-(trifluoromethoxy)-1H-indazole-3-carboxamide;
N-((3R)-1-azabicyclo[2.2.2]oct-3-yl)-5-(trifluoromethoxy)-1H-indazole-3-carboxamide;
N-((3S)-1-azabicyclo[2.2.2]oct-3-yl)-5-(trifluoromethoxy)-1H-indazole-3-carboxamide;
N-(2-((3-pyridinyl)methyl)-1-azabicyclo[2.2.2]oct-3-yl) benzofuran-2-carboxamide;
(2S,3R)—N-(2-((3-pyridinyl)methyl)-1-azabicyclo[2.2.2] oct-3-yl)benzofuran-2-carboxamide;
N-(2-((3-pyridinyl)methyl)-1-azabicyclo[2.2.2]oct-3-yl)-3,5-difluorobenzamide;
(2S,3R)—N-(2-((3-pyridinyl)methyl)-1-azabicyclo[2.2.2] oct-3-yl)-3,5-difluorobenzamide;
N-(2-((3-pyridinyl)methyl)-1-azabicyclo[2.2.2]oct-3-yl)-5-methylthiophene-2-carboxamide;
(2S,3R)—N-(2-((3-pyridinyl)methyl)-1-azabicyclo[2.2.2] oct-3-yl)-5-methylthiophene-2-carboxamide;
N-(2-((3-pyridinyl)methyl)-1-azabicyclo[2.2.2]oct-3-yl)-5-(2-pyridinyl)thiophene-2-carboxamide;
(2S,3R)—N-(2-((3-pyridinyl)methyl)-1-azabicyclo[2.2.2] oct-3-yl)-5-(2-pyridinyl)thiophene-2-carboxamide;
7,8,9,10-tetrahydro-6,10-methano-6H-pyrazino-(2,3-h)(3)-benzazepine;
3-[1-(2,4-Dimethoxy-phenyl)-meth-(E)-ylidene]-3,4,5,6-tetrahydro-[2,3']bipyridinyl;
N-methyl-1-{5-[3'H-spiro[4-azabicyclo[2.2.2]octane-2,2'-furo[2,3-b]pyridin]-5'-yl]-2-thienyl}methanamine;
N-methyl-1-{5-[(2R)-3'H-spiro[4-azabicyclo[2.2.2]octane-2,2'-furo[2,3-b]pyridin]-5'-yl]-2-thienyl}methanamine;
N-methyl-1-{5-[(2S)-3'H-spiro[4-azabicyclo[2.2.2]octane-2,2'-furo[2,3-b]pyridin]-5'-yl]-2-thienyl}methanamine;
(R)-7-chloro-N-(quinuclidin-3-yl)benzo[b]thiophene-2-carboxamide;
5-{5-[(endo)-8-azabicyclo[3.2.1]octan-3-yloxy]pyridin-2-yl}-1H-indole;
5-{5-[(exo)-8-azabicyclo[3.2.1]octan-3-yloxy]pyridin-2-yl}-1H-indole;
5-{5-[(endo)-8-methyl-8-aza-bicyclo[3.2.1]oct-3-yloxy] pyridin-2-yl}-1H-indole;
5-{5-[(exo)-8-methyl-8-aza-bicyclo[3.2.1]oct-3-yloxy]pyridin-2-yl}-1H-indole;
4-{5-[(exo)-8-methyl-8-aza-bicyclo[3.2.1]oct-3-yloxy]pyridin-2-yl}-1H-indole;
5-{6-[(exo)-8-methyl-8-aza-bicyclo[3.2.1]oct-3-yloxy]pyridin-3-yl}-1H-indole;
(2'R)-spiro-[1-azabicyclo[2.2.2]octane-3,2'(3'H)-furo[2,3-b]pyridine];
1,4-Diaza-bicyclo[3.2.2]nonane-4-carboxylic acid 4-bromophenyl ester; and
5-{6-[1-azabicyclo[2.2.2]oct-3-yloxy]pyridazin-3-yl}-1H-indole;
in free base form or in acid addition salt form.

Embodiment 2: An alpha 7 nicotinic acetylcholine receptor agonist according to embodiment 1 for use in the facilitation of emergence from general anesthesia in a subject treated with a general anesthetic agent.

Embodiment 3: An alpha 7 nicotinic acetylcholine receptor agonist according to embodiment 2, wherein the general anesthetic agent is selected from an intravenous anesthetic and an inhalation anesthetic, or a combination thereof.

Embodiment 4: An alpha 7 nicotinic acetylcholine receptor agonist according to embodiment 2, wherein the general anesthetic agent is selected from propofol; etomidate; a barbiturate; a benzodiazepine; ketamine, a halogenated ether, alone or combined with nitrous oxide; halothane; and xenon; or a combination thereof.

Embodiment 5: An alpha 7 nicotinic acetylcholine receptor agonist according to embodiment 2, wherein the general anesthetic agent is a combination of ketamine for the induction period and sevoflurane for the maintenance period.

Embodiment 6: An alpha 7 nicotinic acetylcholine receptor agonist according to embodiment 2, wherein the subject is a perioperative patient.

Embodiment 7: An alpha 7 nicotinic acetylcholine receptor agonist according to embodiment 2, wherein the agonist is administered by intravenous administration.

Embodiment 8: An alpha 7 nicotinic acetylcholine receptor agonist according to embodiment 2, wherein the agonist is administered by intravenous administration when the subject is no longer being treated with the general anesthetic agent.

Embodiment 9: An alpha 7 nicotinic acetylcholine receptor agonist according to embodiment 7, wherein the administration is continuous intravenous infusion within 10 to 60 minutes.

Embodiment 10: An alpha 7 nicotinic acetylcholine receptor agonist according to embodiment 7, wherein the administration is continuous intravenous infusion within 10 to 20 minutes.

Embodiment 11: An alpha 7 nicotinic acetylcholine receptor agonist according to embodiment 7, wherein the daily dosage of the agonist is from 1 to 200 mg.

Embodiment 12: An alpha 7 nicotinic acetylcholine receptor agonist according to embodiment 7, wherein the daily dosage of the agonist is from 10 to 100 mg.

Embodiment 13: An alpha 7 nicotinic acetylcholine receptor agonist according to embodiment 7, wherein the administration is continuous intravenous infusion of 1 to 200 mg of the agonist within 10 to 60 minutes.

Embodiment 14: An alpha 7 nicotinic acetylcholine receptor agonist according to embodiment 1, wherein the agonist is (R)-3-(6-p-tolyl-pyridin-3-yloxy)-1-aza-bicyclo[2.2.2]octane in free base form or in acid addition salt form.

Embodiment 15: An alpha 7 nicotinic acetylcholine receptor agonist according to embodiment 1 for use in the facilitation of emergence from general anesthesia in a subject treated with a general anesthetic agent;
wherein the general anesthetic agent is selected from propofol; etomidate; a barbiturate; a benzodiazepine; ketamine, a halogenated ether, alone or combined with nitrous oxide; halothane; and xenon; or a combination thereof;
wherein the subject is a perioperative patient; and
wherein the administration is continuous intravenous infusion within 10 to 60 minutes.

Embodiment 16: An alpha 7 nicotinic acetylcholine receptor agonist according to embodiment 15, wherein the agonist is (R)-3-(6-p-tolyl-pyridin-3-yloxy)-1-aza-bicyclo[2.2.2]octane in free base form or in acid addition salt form.

Embodiment 17: An alpha 7 nicotinic acetylcholine receptor agonist according to embodiment 16, wherein the administration is continuous intravenous infusion of 1 to 200 mg of the agonist within 10 to 60 minutes.

Embodiment 18: Use of an alpha 7 nicotinic acetylcholine receptor agonist as defined in embodiment 1 for the facilitation of emergence from general anesthesia.

Embodiment 19: A method of facilitation of emergence from general anesthesia in a subject treated with an general anesthetic agent which comprises administering to said subject an effective amount of an alpha 7 nicotinic acetylcholine receptor agonist as defined in embodiment 1.

Embodiment 20: Use of an alpha 7 nicotinic acetylcholine receptor agonist as defined in embodiment 1 for the preparation of a medicament for the facilitation of emergence from general anesthesia.

Embodiment 21: A kit comprising an alpha 7 nicotinic acetylcholine receptor agonist as defined in embodiment 1 and instructions for using the agonist in the facilitation of emergence from general anesthesia in a subject treated with an general anesthetic agent.

Embodiment 22: A pharmaceutical composition for intravenous administration comprising
an alpha 7 nicotinic acetylcholine receptor agonist as defined in embodiment 1; and
at least one pharmaceutically acceptable excipient.

Embodiment 23: A pharmaceutical composition in the form of an aqueous solution for intravenous administration comprising
an alpha 7 nicotinic acetylcholine receptor agonist as defined in embodiment 1; and
at least one pharmaceutically acceptable excipient.

Embodiment 24: A pharmaceutical composition in the form of an aqueous solution for intravenous administration comprising
from 0.5 to 50 mg of an alpha 7 nicotinic acetylcholine receptor agonist as defined in embodiment 1; and
at least one pharmaceutically acceptable excipient.

The following non-limiting examples are illustrative of the disclosure.

Formulation Example:

The below is an example of a pharmaceutical composition comprising an alpha 7 nicotinic acetylcholine receptor agonist of the invention for intravenous administration.

| | | |
|---|---|---|
| α7 nAChR agonist of the invention | 2.5 mg | 25 mg |
| NaCl | 18 mg | 15 mg |
| 0.01N NaOH or HCl for pH adjustment | q.s. | q.s. |
| Water for injection up to | 2.0 ml | 2.0 ml |

Biological Examples:

The usefulness of α7 nAChR agonists of the invention in the facilitation of emergence from general anesthesia can be confirmed in a range of standard tests including those indicated below.

1. Preclinical Testing (In Vivo Pharmacology)

1.1 Orexin-Deficiency Model:

a) Animals

Male transgenic mice with a knockout of the orexin peptide gene are used. Orexin-deficient mice express a phenotype with cataplexy events (observed as 'behavioral arrests') and a disrupted sleep pattern including fragmented sleep and sleepiness in their active period.

b) Assessment of Behavior

The animals are observed and videotaped via infrared cameras during the first hours of the lights-off period which is the active phase of nocturnal rodents like mice. At this time, orexin-deficient mice show the most 'behavioral arrests'. The number of these events can be furthermore increased by presenting a new environment. For this purpose, new saw dust, a running wheel, marbles and tunnels are placed in the test environment. The number of 'behavioral arrests' are offline counted by the experimenter for each hour of recording. Behavioral arrests were defined by phases of total inactivity outside the next box, which last longer than 10 second, preceded and followed by robust locomotor activity (see also Scammell et al., 2009, Sleep 32(1): 111-116). Some of the animals have temporal skull EEG electrodes implanted which are connected to transmitters. The EEG is recorded via a receiver and stored on a PC for further analysis. EEG is used to assess and to quantify sleep behavior and vigilance stage.

c) Protocol

A cross-over design is used because of the high inter- and intra-individual variability of the behaviors to be observed. Furthermore, to avoid habituation to the test environment, the animals are only tested once per week in the test environment. During the remaining days, the animals are in their homecage.

For each experimental session, 3-4 mice are put into the test environment 3 hours before lights-off. The first experimental session (week 1) is used to get a baseline (without treatment). The second and third sessions (weeks 2+3) are used for treatment (vehicle & compound, cross-over design, administration 5 minutes before lights-off). The fourth and last experimental session is again without treatment to evaluate a post-treatment baseline.

d) Results

FIG. 1 depicts the effects of 3 mg/kg compound B-4, orally administered directly before lights-off, on the number of narcoleptic episodes (behavioral arrests) in orexin-deficient mice. Compound B-4 decreased the number of narcoleptic episodes during the whole 4 hours observation period by ca. 25% (Paired t-test: $t_{14}=2.48$, p=0.03; FIGS. 1A+B). The reduction was more pronounced during the first hour (ca. 47%; $t_{14}=2.32$, p=0.04; FIG. 1C).

Figure 2:
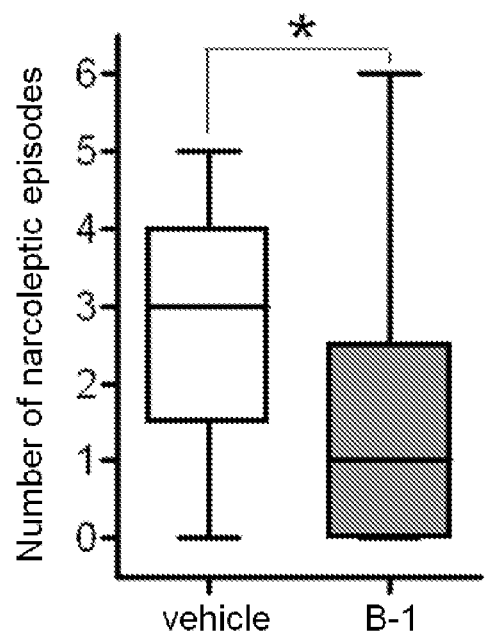
FIG. 2 depicts the effects of 10 mg/kg compound B-1, orally administered directly before lights-off, on the number of narcoleptic episodes (behavioral arrests) in orexin-deficient mice.

FIG. 2 depicts the effects of 10 mg/kg compound B-1, orally administered directly before lights-off, on the number of narcoleptic episodes (behavioral arrests) in orexin-deficient mice. Compound B-1 significantly decreased the number of narcoleptic episodes during the first hour of the observation period by ca. 66% (p<0.05 Anova).

1.2 EEG Data a) Animals

Animals have temporal skull EEG electrodes implanted which are connected to transmitters. Animals were group-housed (2-4) per cage at a constant temperature of 22±1° C., on a 12:12 light-dark schedule. The EEG is recorded via a receiver and stored on a PC for further analysis. EEG is used to assess and to quantify sleep behavior and vigilance stage.

b) Protocol

Animals were given a 1-day period of acclimatization in the recording cages with recording cables connected. On the 1st day of the experiment, EEG recordings were made continuously during a 22-hours period beginning at 11 A.M., 15 min after vehicle administration. On the second day of the experiment, EEG recordings were carried out in the same way, but 15 minutes after drug administration. In this way, each animal served as its own control. 10 animals were recorded from simultaneously in each experiment. Automatic evaluation of the nycthemeral cycle (REM sleep, classical sleep, wakefulness and an awake non-vigilant state termed "drowsiness") was performed as described (Vigouret et al., 1978 Pharmacology 16 Suppl 1:156-73). In the present context, "quiet wake" and "active wake", describe conscious animals in a resting and an active state, respectively, while "REM" and "NREM" represent sleep states.

c) Results

Figure 3:
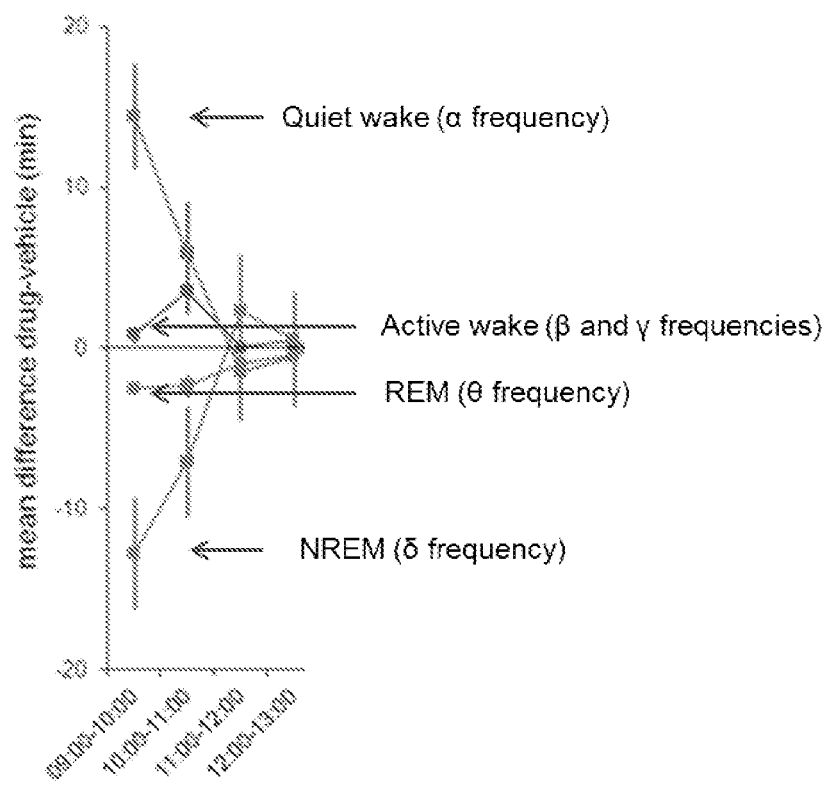
FIG. 3 depicts the effects on EEG measurements after 30 mg/kg of compound B-1, orally administered 6 h after lights on in mice, on quiet wake, active wake, REM sleep, and NREM sleep.

FIG. 3 depicts the effects of 30 mg/kg compound B-1, orally administered 6 h after lights on (9:00) in mice (n=10) on quiet wake (α frequency, 9.5-12.5 Hz), active wake (β frequency, 12.5-30.5 Hz; and γ frequency, >30.5 Hz), REM sleep (θ frequency, 4.5-9.5 Hz) and NREM sleep (δ frequency, <4.5 Hz). Assessment period shown is 3 hours. Compound B-1 causes a decline of NREM sleep and increases the time spent in quiet wake. The numerical assessment of FIG. 3 is given in table 1.

TABLE 1

|  | Mean difference drug-vehicle (min) assessed at time point | | | |
| --- | --- | --- | --- | --- |
|  | 9:30 | 10:30 | 11:30 | 12:30 |
| Quiet wake (α frequency) | 14.3 | 6.1 | −1.8 | −0.9 |
| Active wake (β and γ frequencies) | 0.9 | 3.6 | 0.1 | 0.3 |
| REM (θ frequency) | −2.2 | −2.1 | −0.9 | −0.2 |
| NREM (δ frequency) | −12.4 | −7.1 | 2.1 | −0.1 |

1.3 Telemethyl Histamine

Histamine (HA) is released all over the brain by tuberomammillary nucleus neurons. Evidence indicates that histaminergic neurons have a major role in wakefulness control. HA is metabolized by histamine-N-methyltransferase to tele-methylhistamine (tMHA) in some tissues, including brain.

a) Protocol

Mice (n=8) were treated during the first hour of the lights-on period and sacrificed 30 min later. Brain tissue was collected and subjected to LC-MS analysis (Croyal et al. Analytical Biochemistry, 2011, 409:28-36) to determine t-MHA levels.

b) Results

Figure 4:
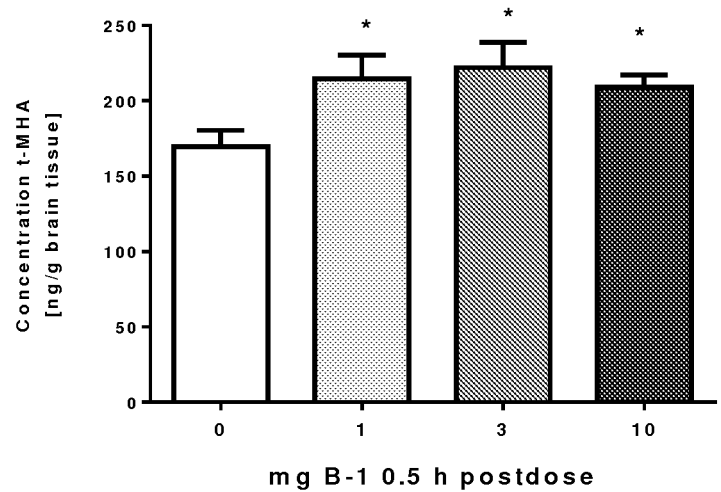
FIG. 4 depicts the effects of different doses of compound B-1 and A-1, orally administered to mice, 30 minutes after administration on brain telemethyl histamine (tMHA) levels.
Figure 4:
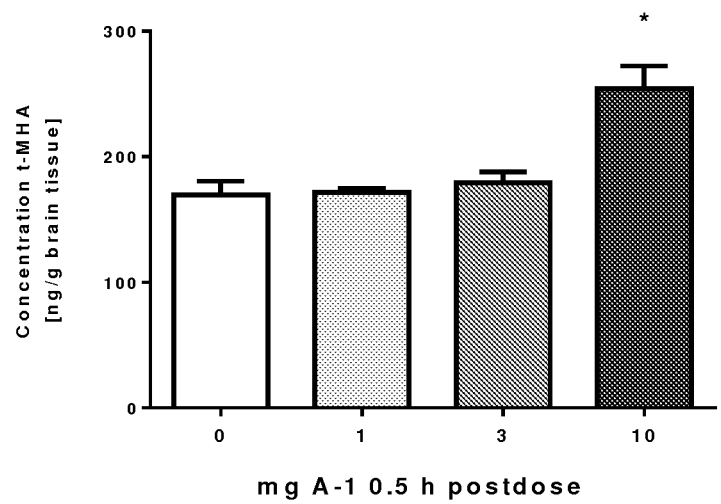

FIG. 4 depicts the effects of different doses of compound B1 and A-1, orally administered to mice, 30 minutes after administration on brain tMHA levels. tMHA levels are significantly elevated for compound B-1 at all doses tested. For compound A-1, a significant elevation is seen for the 10 mg/kg dose.

1.4 Signs for Emergence of Anesthesia in Nonhuman Primates

Clear signs for emergence from general anesthesia after administration of an α7 nAChR agonist of the invention at a therapeutically relevant dose were seen in a positron emission tomography (PET) experiment otherwise unrelated to this disclosure. Said experiment was performed on the α7 nAChR in the non-human primate (NHP) brain. Said experiment resulted in relevant data on the effect of compound A-1 in non-human primates anesthesized with ketamine/sevoflurane.

a) Methods:

An animal (Cynomolgus monkey, male, 5.8 kg) was anesthesized for the entire duration of the PET experiment, i.e. for approximately 7.5 hours. Due to the nature of these experiments, it is crucial that anesthesia is maintained.

General anesthesia was induced by i.m. injection of ketamine hydrochloride (10 mg/kg, Ketaminol, Intervet AB). The animal was intubated and general anesthesia was maintained by inhalational administration of sevoflurane (1.5-8%, Abbott Scandinavia AB). Body temperature was maintained by Bair Hugger Model 505 (Arizant Healthcare Inc., Eden Prairie, Minn., USA). ECG, pulse, blood pressure, respiration rate, oxygen saturation and tidal $CO_2$ level were monitored continuously during the experiment. Ventilation of the animal (breathing frequency and volume) was controlled by machine during the general anesthesia. The animal underwent two consecutive PET scans. The PET ligand was administered i.v. at doses too low to have a pharmacodynamic effect (i.e. total dose of 0.16 and 0.25 μg). Before the start of the second PET scan, 10 mg/kg of compound A-1 was administered to the animal using an oral gavage tube.

b) Observations:

No remarkable observations were made before/during/after administration of the PET ligand and during the PET scan. By completion of the first scan, anesthesia had successfully been maintained for about three hours by administration of 2.6-2.9% sevoflurane.

Fifteen minutes after administration of compound A-1, surprisingly, shallow breathing was observed in the NHP, indicating that the animal did not accept the controlled breathing, but was trying to breath spontaneously in a potentially irregular pattern. This change in breathing behavior is a clear sign for emergence from general anesthesia.

As it was crucial to maintain anesthesia, the dose of sevoflurane was immediately increased 1.7-fold (from 2.9% to 5%). The breathing behavior reverted directly to machine-controlled breathing with no shallow breathing, i.e. an anesthesia-like breathing behaviour.

As a few minutes later a drop in blood pressure was observed. Hypotension is a known adverse event with sevoflurane in humans. Therefore, the dose of sevoflurane was decreased (from 5% to 3.7%). Shortly afterwards these changes in vitals spontaneously reverted and no further intervention was necessary. For the rest of the experiment (about two hours) anesthesia was successfully maintained, however higher doses of sevoflurane (3.0-3.7%) were necessary than during the first half of the experiment.

c) Conclusions:

In-life observations indicated awakening of the animal form anesthesia shortly after the administration of compound A-1, which indicates that compound A-1 may cause emergence from general anesthesia.

2. Clinical Testing:

Clinical testing of the α7 nAChR agonist of the invention may be conducted, for example, in the following study design. The skilled physician may look at a number of aspects of patient behaviors and abilities. He will realize that such study is considered as guidelines and the certain aspects of the study may be modified and redefined depending on the circumstance and environment, for example.

Elective surgery patients requiring general anesthesia (e.g. total intravenous anesthesia, and/or use of inhalation anesthetics) are dosed with an α7 nAChR agonist of the invention i.v.

Different aspects may be analyzed after administration of the α7 nAChR agonist of the invention such as time to emerge from anesthesia (e.g. when the subject is (i) conscious, (ii) able to answer simple questions, (iii) able to make voluntary movements, (iv) maintains adequate ventilation and (v) is able to protect his airways) and/or incidence of complications. Examples of complications include e.g. laryngospasm, respiratory depression, hemodynamic instability, anesthesia-related delirium, agitation (especially in children), vomiting, aspiration pneumonia and postoperative Cognitive Dysfunction (POCD).

The patients are tested against placebo and/or standard of care and the results are compared and analyzed.

In some embodiments, provided herein are methods for increasing the amount of consciousness or mental cognitive functioning of an unconscious subject wherein the subject is unconscious by general anesthesia, comprising administering to the subject an α7 nAChR agonist of the invention.

The invention also provides a kit comprising an α7 nAChR agonist of the invention and instructions for using the agonist in the facilitation of emergence from general anesthesia in a subject treated with an general anesthetic agent.

What is claimed is:

1. A method of facilitating emergence from general anesthesia, comprising:
administering to a subject who has previously been treated with a general anesthetic agent, a therapeutically effective amount of (R)-3-(6-p-tolyl-pyridin-3-yloxy)-1-aza-bicyclo[2.2.2]octane in free base form or acid addition salt form.

2. The method of claim 1, wherein the general anesthetic agent is selected from an intravenous anesthetic, an inhalation anesthetic, and a combination thereof.

3. The method of claim 2, wherein the anesthetic agent is an intravenous anesthetic, and is selected from the group consisting of: propofol, etomidate, a barbiturate, a benzodiazepine, and ketamine.

4. The method of claim 2, wherein the anesthetic agent is an inhalation anesthetic, and is selected from the group consisting of: a halogenated ether, a halogenated ether in combination with nitrous oxide, halothane, and xenon.

5. The method of claim 1, wherein the general anesthetic agent is a combination of ketamine for an induction period and sevoflurane for a maintenance period.

6. The method of claim 1, further comprising:
intravenously administering the (R)-3-(6-p-tolyl-pyridin-3-yloxy)-1-aza-bicyclo [2.2.2]octane to the subject while concurrently administering the general anesthetic agent to the subject.

7. The method of claim 6, further comprising:
concurrently increasing a dose of the (R)-3-(6-p-tolyl-pyridin-3-yloxy)-1-aza-bicyclo[2.2.2]octane while reducing a dose of the general anesthetic agent.

8. The method of claim 1, further comprising:
administering the general anesthetic agent to the subject; and
commencing intravenously administering the (R)-3-(6-p-tolyl-pyridin-3-yloxy)-1-aza-bicyclo[2.2.2]octane to the subject at or after a time at which the administering of the general anesthetic agent to the subject ceases.

9. The method of claim 1, further comprising:
intravenously administering the (R)-3-(6-p-tolyl-pyridin-3-yloxy)-1-aza-bicyclo[2.2.2]octane to the subject in an amount of 1 to 200 mg within 10 to 60 minutes.

* * * * *